US010909328B2

(12) United States Patent
Takano et al.

(10) Patent No.: US 10,909,328 B2
(45) Date of Patent: Feb. 2, 2021

(54) SENTIMENT ADAPTED COMMUNICATION

(71) Applicant: International Business Machines Corporation, Armonk, NY (US)

(72) Inventors: Sawa Takano, Chiba (JP); Tadayuki Yoshida, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 135 days.

(21) Appl. No.: 16/239,596

(22) Filed: Jan. 4, 2019

(65) Prior Publication Data

US 2020/0218781 A1 Jul. 9, 2020

(51) Int. Cl.
*G06F 40/40* (2020.01)
*A61B 5/16* (2006.01)
(Continued)

(52) U.S. Cl.
CPC .............. *G06F 40/40* (2020.01); *A61B 5/165* (2013.01); *G06K 9/00302* (2013.01);
(Continued)

(58) Field of Classification Search
CPC .... G06F 40/40; G06F 17/2785; G06F 17/279; G06F 17/28; G06K 9/00302; G10L 15/1822; G10L 15/265; G10L 17/26; G10L 25/63; G10L 2015/226; G06N 20/00; G06N 5/003; G06Q 30/0201; G06Q 50/01; G06Q 30/016; A61B 5/165
See application file for complete search history.

(56) References Cited

U.S. PATENT DOCUMENTS 7,865,354 B2 * 1/2011 Chitrapura .............. G06F 40/30
704/4
8,237,742 B2 * 8/2012 Basson ................ G11B 27/028
345/629

(Continued)

OTHER PUBLICATIONS

P. Mell, et al. "*The NIST Definition of Cloud Computing*", NIST Special Publication 800-145, Sep. 2011, Gaithersburg, MD.

*Primary Examiner* — Mohammad K Islam
(74) *Attorney, Agent, or Firm* — Robert Shatto, Esq.; George S. Blasiak, Esq.; Heslin Rothenberg Farley & Mesiti P.C.

(57) ABSTRACT

Methods, computer program products, and systems are presented. The method computer program products, and systems can include, for instance: examining communication data of a first human user to return one or more sentiment attribute of the communication data; processing the communication data to return sentiment neutral adapted communication data, the processing being in dependence on the one or more sentiment attribute; presenting to a second human user a sentiment neutral adapted communication, the sentiment neutral adapted communication being based on the sentiment neutral adapted communication data; augmenting second communication data to return adapted second communication data, the augmenting being in dependence of the one or more sentiment attribute; and presenting to the first human user an adapted second communication, the adapted second communication being based on the adapted second communication data.

20 Claims, 11 Drawing Sheets

(51) Int. Cl.
*G06Q 30/00* (2012.01)
*G10L 17/26* (2013.01)
*G10L 15/18* (2013.01)
*G06K 9/00* (2006.01)
*G10L 25/63* (2013.01)
*G10L 15/26* (2006.01)
*G10L 15/22* (2006.01)

(52) U.S. Cl.
CPC ........ *G06Q 30/016* (2013.01); *G10L 15/1822* (2013.01); *G10L 15/26* (2013.01); *G10L 17/26* (2013.01); *G10L 25/63* (2013.01); *G10L 2015/226* (2013.01)

(56) References Cited

U.S. PATENT DOCUMENTS

| | | | |
|---|---|---|---|
| 8,259,992 B2* | 9/2012 | Basson | G10L 19/167 382/100 |
| 9,117,446 B2* | 8/2015 | Bao | G10L 13/02 |
| 9,177,554 B2* | 11/2015 | Bhatt | G10L 15/26 |
| 9,189,879 B2* | 11/2015 | Filev | A61B 5/744 |
| 9,460,083 B2* | 10/2016 | Fink | G06F 40/30 |
| 9,665,567 B2* | 5/2017 | Liu | G06F 3/011 |
| 9,690,775 B2* | 6/2017 | Fink | G06F 40/30 |
| 9,996,217 B2* | 6/2018 | Kozloski | G06F 40/186 |
| 10,008,196 B2 | 6/2018 | Maisonnier et al. | |
| 10,037,768 B1* | 7/2018 | Akkiraju | H04M 3/2236 |
| 2009/0313015 A1* | 12/2009 | Basson | G10L 19/167 704/236 |
| 2013/0157666 A1 | 6/2013 | Uchino | |
| 2014/0178970 A1 | 6/2014 | Vanzin | |
| 2014/0188459 A1* | 7/2014 | Fink | G06F 40/30 704/9 |
| 2014/0270109 A1 | 9/2014 | Riahi et al. | |
| 2016/0140985 A1* | 5/2016 | Basson | G11B 27/028 704/271 |
| 2017/0125008 A1* | 5/2017 | Maisonnier | B25J 11/0005 |
| 2018/0047029 A1 | 2/2018 | Saso et al. | |
| 2018/0226073 A1* | 8/2018 | Hodge | G10L 15/1822 |
| 2020/0143329 A1* | 5/2020 | Gamaliel | G06K 9/00288 |

* cited by examiner

SENTIMENT ADAPTED COMMUNICATION

BACKGROUND

Sentiment analysis can include use of Natural Language Processing (NLP), text mining, linguistics or biometrics to identify affective states of individuals. Language content can be subject to processing by Natural Language Processing (NLP) for return of sentiment parameter values for a variety of different sentiment parameters such as "anger," "disgust," "fear," "joy," and/or "sadness". Both vocal utterance based and text based content can be subject to processing by NLP.

Data structures have been employed for improving operation of computer systems. A data structure refers to an organization of data in a computer environment for improved computer system operation. Data structure types include containers, lists, stacks, queues, tables and graphs. Data structures have been employed for improved computer system operation e.g. in terms of algorithm efficiency, memory usage efficiency, maintainability, and reliability.

Artificial intelligence (AI) refers to intelligence exhibited by machines. Artificial intelligence (AI) research includes search and mathematical optimization, neural networks and probability. Artificial intelligence (AI) solutions involve features derived from research in a variety of different science and technology disciplines ranging from computer science, mathematics, psychology, linguistics, statistics, and neuroscience.

SUMMARY

Shortcomings of the prior art are overcome, and additional advantages are provided, through the provision, in one aspect, of a method. The method can include, for example: examining communication data of a first human user to return one or more sentiment attribute of the communication data; processing the communication data to return sentiment neutral adapted communication data, the processing being in dependence on the one or more sentiment attribute; presenting to a second human user a sentiment neutral adapted communication, the sentiment neutral adapted communication being based on the sentiment neutral adapted communication data; augmenting second communication data to return adapted second communication data, the augmenting being in dependence of the one or more sentiment attribute; and presenting to the first human user an adapted second communication, the adapted second communication being based on the adapted second communication data.

In another aspect, a computer program product can be provided. The computer program product can include a computer readable storage medium readable by one or more processing circuit and storing instructions for execution by one or more processor for performing a method. The method can include, for example: examining communication data of a first human user to return one or more sentiment attribute of the communication data; processing the communication data to return sentiment neutral adapted communication data, the processing being in dependence on the one or more sentiment attribute; presenting to a second human user a sentiment neutral adapted communication, the sentiment neutral adapted communication being based on the sentiment neutral adapted communication data; augmenting second communication data to return adapted second communication data, the augmenting being in dependence of the one or more sentiment attribute; and presenting to the first human user an adapted second communication, the adapted second communication being based on the adapted second communication data.

In a further aspect, a system can be provided. The system can include, for example a memory. In addition, the system can include one or more processor in communication with the memory. Further, the system can include program instructions executable by the one or more processor via the memory to perform a method. The method can include, for example: examining communication data of a first human user to return one or more sentiment attribute of the communication data; processing the communication data to return sentiment neutral adapted communication data, the processing being in dependence on the one or more sentiment attribute; presenting to a second human user a sentiment neutral adapted communication, the sentiment neutral adapted communication being based on the sentiment neutral adapted communication data; augmenting second communication data to return adapted second communication data, the augmenting being in dependence of the one or more sentiment attribute; and presenting to the first human user an adapted second communication, the adapted second communication being based on the adapted second communication data.

Additional features are realized through the techniques set forth herein. Other embodiments and aspects, including but not limited to methods, computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
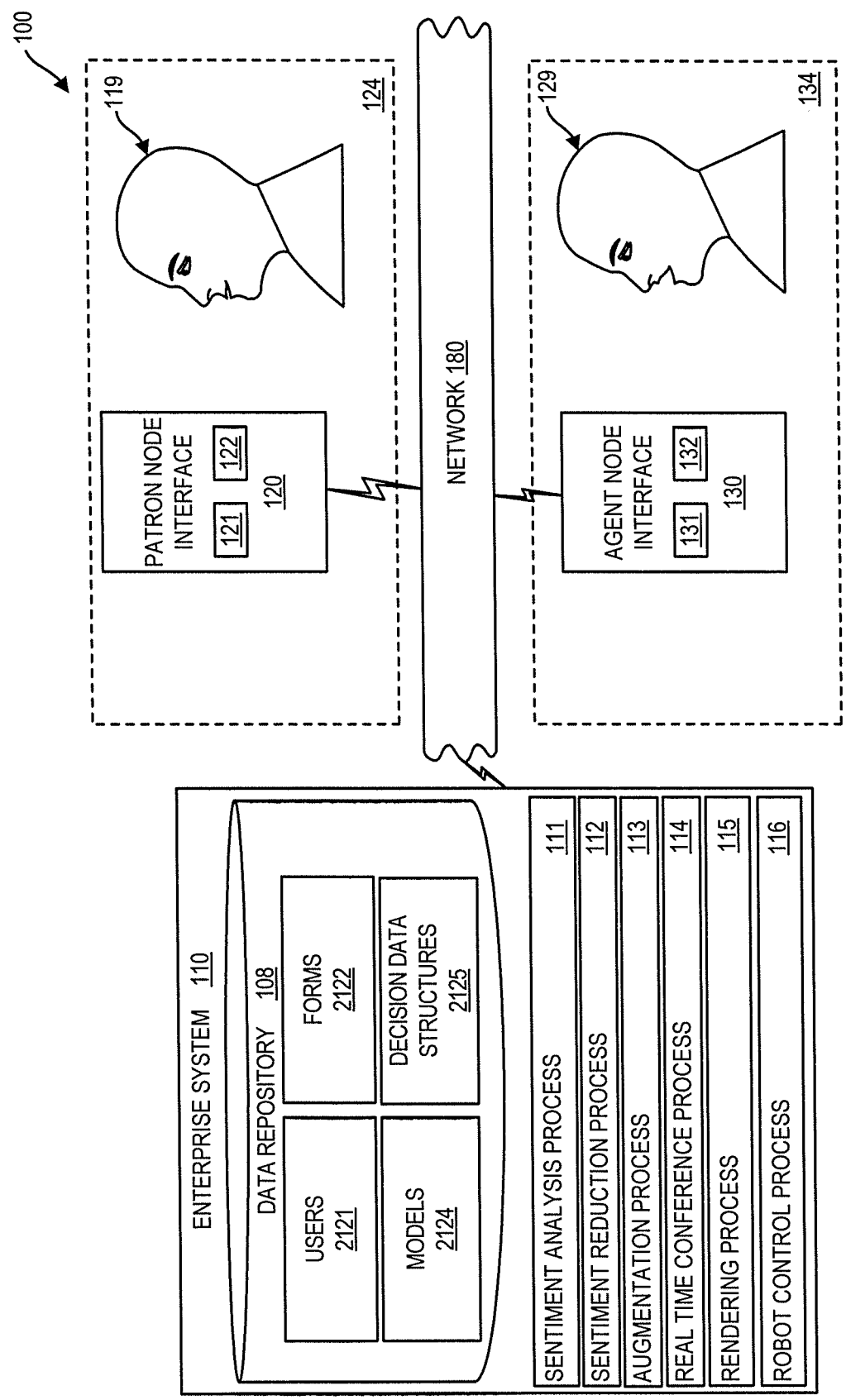
FIG. 1 is a block diagram of a system having an enterprise system, a patron node interface, and an agent node interface in communication with one another via network according to one embodiment.

System 100 for enhanced user and computer system interactions is shown in FIG. 1. System 100 can include enterprise system 110 having an associated data repository 108, patron node interface 120, and agent node interface 130. Enterprise system 110, patron node interface 120, and agent node interface 130 can be in communication with one another via network 180. System 100 can include numerous devices which can be computing node based devices connected by network 180. Network 180 may be a physical network and/or a virtual network. A physical network can be, for example, a physical telecommunications network connecting numerous computing nodes or systems, such as computer servers and computer clients. A virtual network can, for example, combine numerous physical networks or parts thereof into a logical virtual network. In another example, numerous virtual networks can be defined over a single physical network.

According to on embodiment, enterprise system 110 can be external and remote from each of patron node interface 120 and agent node interface 130. According to one embodiment, enterprise system 110 can be collocated with one or more of patron node interface 120 and/or agent node interface 130.

Referring further to FIG. 1 patron node interface 120 can include one or more input device 121 and one or more output device 122. The one or more input device can include, e.g. an audio input device and/or a video input device, e.g. a camera sensor. The one or more output device 122 can include, e.g. an audio speaker and one or more video and text output device, e.g. a display. Agent node interface 130 can include one or more input device 131 and one or more output device 132. The one or more input device can include, e.g. an audio input device and/or a video input device, e.g. a camera sensor. The one or more output device 132 can include, e.g. one or more audio output device, e.g. an audio speaker and one or more video and text output device, e.g. a display.

In a patron environment 124 there can be included a patron user 119 who interacts with patron node interface 120. Patron user 119 can be a human user. In agent environment 134 there can be included an agent user 129 who interacts with agent node interface 130. Agent user 129 can be a human user. Patron node interface 120 can include, e.g. a mechanical robot and/or client computer device, e.g. a PC or a mobile client computer device, e.g. a laptop, tablet, smartphone, smartwatch. Agent node interface can include, e.g. a client computer device such as a PC or a mobile client computer device, e.g. a laptop, tablet, smartphone, smartwatch.

Embodiments herein recognize that data records in respect to a patron user interacting with an enterprise providing services to a patron user can include significant errors. Embodiments herein recognize that a patron user interacting with an enterprise can be characterized by the patron exhibiting heightened sentiment parameter values across a variety of different sentiment classifications and that in such scenarios an agent such as a human agent of the enterprise can exhaust his or her attention to moderating the heightened emotional state of the patron, rather than on the creation of accurate electronic records based on factual data received from the patron user. Embodiments herein can process communication data of a patron user to identify heightened sentiment content thereof to adapt patron communication data into a sentiment neutral form for consumption by an enterprise agent user. Communications from an enterprise to the patron can be sentiment augmented communications that are augmented in a manner in dependence on the patron user's emotional state which can be indicated by exhibited sentiment parameter values of the patron user.

Data repository 108 of enterprise system 110 can store various data. In users area 2121 of data repository 108 data repository 108 can store data on patron users of system 100. Users can include, e.g. registered patron users or unregistered guest patron users. Within users area 2121 there can be stored such data as historical records of prior communication sessions with patron users, session data of current communication sessions with patron users, session data of items or services of an enterprise consumed by patron users, and speech profile data of respective patron users that specifies characteristics of the respective patron user's speech. Enterprise system 110 can use such speech profile data for recognizing a patron as a certain patron having a profile stored in users area 2121 and for recognizing attributes, e.g. sentiment parameter values of a patron user's speech. As noted, data repository 108 in users area 2121 can store session data on communication sessions engaged in by users of system 100. Session data can include communication data of patron users and enterprise agent users, adapted communications, action decisions, and returned sentiment parameter value data sets associated to segments of communication data.

Data repository 108 in forms area 2122 can store forms for use by an enterprise in conducting a communication session with a patron user. Forms of forms area 2122 can include, e.g. lists of content which an enterprise should collect when interacting with a patron user in a communication session. Such information in the case where a physical product item is the subject of a communication session can include, e.g. item ID number, item version number, patron name, patron ID, time of the problem, response deadline, nature of an inquiry, effect of a problem, and the like.

Data repository 108 in models area 2123 can store data on models for use by system 100 in the return of actions decisions. Models stored in models area 2123 can include, e.g. predictive models that are trained using machine learning training processing such as supervised machine learning processes.

Data repository 108 in decision data structures area 2124 can store decision data structures for use by system 100 in the return of action decisions. Decision data structures can include, e.g. action decision tables and/or decision trees. According to one embodiment data repository 108 in decision data structures area 2124 can store a decision data structure that cognitively maps an emotional state of a patron user to communication action decisions such as gesture action decisions which may be presented, e.g. by a intelligent agent controlling a physical robot or humanoid form virtual agent, and/or speech action decisions wherein certain speech is selected for presentment to a patron user in dependence on a patron users exhibited emotional state, e.g. the most recently exhibited emotional state of a patron user.

Enterprise system 110 can run various processes including sentiment analysis process 111, sentiment reduction process 112, augmentation process 113, real time conference process 114, rendering process 115, and robot control process 116.

Enterprise system 110 can run sentiment analysis process 111 for return of sentiment parameters values for various sentiment parameters such as "anger," "disgust," "fear,"

"joy," and/or "sadness". Enterprise system 110 running sentiment analysis process 111 can include enterprise system running a Natural Language Processing (NLP) process for determining one or more NLP output parameter of a message. Enterprise system 110 according to one embodiment can return sentiment parameter values on a scale of 0.0 to 1.0 with the values indicating the likelihood (probability) that the sentiment is present. Enterprise system 110 running an NLP process can include one or more of a topic classification process that determines topics of messages and output one or more topic NLP output parameter, a sentiment analysis process which determines sentiment parameter for a message, e.g. polar sentiment NLP output parameters, "negative," "positive," and/or non-polar NLP output sentiment parameters, e.g. "anger," "disgust," "fear," "joy," and/or "sadness" or other classification process for output of one or more other NLP output parameters e.g. one of more "social tendency" NLP output parameter or one or more "writing style" NLP output parameter.

By running of an NLP process enterprise system 110 can perform a number of processes including one or more of (a) topic classification and output of one or more topic NLP output parameter for a received message (b) sentiment classification and output of one or more sentiment NLP output parameter for a received message or (c) other NLP classifications and output of one or more other NLP output parameter for the received message.

Topic analysis for topic classification and output of NLP output parameters can include topic segmentation to identify several topics within a message. Topic analysis can apply a variety of technologies e.g. one or more of Hidden Markov model (HMM), artificial chains, passage similarities using word co-occurrence, topic modeling, or clustering. Sentiment analysis for sentiment classification and output of one or more sentiment NLP parameter can determine the attitude of a speaker or a writer with respect to some topic or the overall contextual polarity of a document. The attitude may be the author's judgment or evaluation, affective state (the emotional state of the author when writing), or the intended emotional communication (emotional effect the author wishes to have on the reader). In one embodiment sentiment analysis can classify the polarity of a given text as to whether an expressed opinion is positive, negative, or neutral. Advanced sentiment classification can classify beyond a polarity of a given text. Advanced sentiment classification can classify emotional states as sentiment classifications. Sentiment classifications can include the classification of "anger," "disgust," "fear," "joy," and "sadness."

Enterprise system 110 running an NLP process can include enterprise system 110 returning NLP output parameters in addition to those specification topic and sentiment, e.g. can provide sentence segmentation tags, phrase tags, word tags, and part of speech tags. Enterprise system 110 can use sentence segmentation parameters to determine e.g. that an action topic and an entity topic are referenced in a common sentence for example.

Enterprise system 110 running sentiment analysis process 111 can include enterprise system 110 processing received patron communication data that is defined by vocal utterance data and/or text data. For processing of vocal utterance data, enterprise system 110 can activate a speech-to-text converter and then process the returned text. Speech-to-text services can be utilized for conversion of speech-to-text. According to one embodiment, IBM® WATSON® speech-to-text services can be utilized (IBM® and WATSON® are registered trademarks of International Business Machines Corporation).

Enterprise system 110 running sentiment analysis process 111 to process vocal utterance data can include in addition or alternatively enterprise system 110 processing received vocal utterance data to examine acoustic characteristics of the vocal utterance data in using a mapping process to map sentiments classifications into identified acoustic characteristics. Acoustic characteristics of different sentiments can include use of the mapping decision data structure of Table A, wherein acoustic characteristics of vocal utterances are mapped to exhibited sentiments.

TABLE A

|  | Fear | Anger | Sadness | Happiness | Disgust |
| --- | --- | --- | --- | --- | --- |
| Speech Rate | Much Faster | Slightly Faster | Slightly Slower | Faster or Slower | Very Much Slower |
| Pitch Average | Very Much Higher | Very Much Higher | Slightly Lower | Much Higher | Very Much Lower |
| Pitch Range | Much Wider | Much Wider | Slightly Narrower | Much Wider | Slightly Wider |
| Intensity | Normal | Higher | Lower | Higher | Lower |
| Voice Quality | Irregular Voicing | Breathy Chest Tone | Resonant | Breathy Blaring | Grumbled Chest Tone |
| Pitch Changes | Normal | Abrupt On Stressed Syllables | Downward Inflection | Smooth Upward Inflections | Wide Downward Terminal Inflections |
| Articulation | Precise | Tense | Slurring | Normal | Normal |

When using acoustic characteristics of vocal utterances to return sentiment classifications, enterprise system 110 can use speech profile data of users area 2121. For example, speech profile data of users area 2121 can include data specifying baseline characteristics of a certain user's speech, from which relative parameters can be returned, e.g. what is regarded to be "faster" speech can be determined in reference to a baseline speech rate for a particular user and therefore can be determined differently depending on which user is speaking.

Enterprise system 110 can run sentiment analysis process 111 to determine sentiment parameter values associated with language content e.g. spoken words or text based words entered e.g. typed into a user interface by a patron user. Enterprise system 110 running sentiment analysis process 111 according to another embodiment in addition or alternatively can process video conference video data representing facial features and based on the processing of the video data can determine an exhibited sentiment associated with the person represented in the video data. Enterprise system 110 running sentiment analysis process 111 can include enterprise system 110 processing of facial feature representing video data for sentiment classification. Determined sentiment parameters can include e.g. a polar sentiment parameters, "negative," "positive," and/or non-polar sentiment parameters, e.g. "anger," "disgust," "fear," "sadness" and/or "joy." In one embodiment sentiment analysis process 111 for providing sentiment classification based on processing of facial feature representing video data can run EMOTION VIDEO ANALYTICS™ software by nVISO™ of Lausanne, Switzerland available on IBM SmartCloud® services (IBM SmartCloud® is a registered trademark of International Business Machines Corporation). Enterprise system 110 running sentiment analysis process 111 can determine a sentiment parameter-value dataset for content and can tag the content with metadata provided by the dataset.

Enterprise system 110 running sentiment reduction process 112 can include enterprise system 110 identifying heightened sentiment content of communication data received from a patron user, can include enterprise system 110 providing adapted patron communication data for sending to an enterprise agent user 129, e.g. a human agent of the enterprise, the adapted communication data being adapted by being subject to sentiment reduction. For reducing the heightened sentiment content of received communication data of a patron, enterprise system 110 can perform various processes. For example, enterprise system 110 for reducing heightened sentiment content can identify an emotional phrase included with received communication data and can substitute such emotional phrase with a null phrase (the absence of content) or a sentiment neutral phrase.

Enterprise system 110 for providing a sentiment adapted communication data having reduced sentiment can include enterprise system 110 presenting vocal utterance data defining received patron communication data and expressing such data as text communication content and/or as synthesized voice communication content that is absent of acoustical characteristics of the received vocal utterance content yielding returned sentiment classifications. Embodiments herein recognize that by representing received vocal utterance data as text or as synthesized voice data, the adapted content can be presented without, e.g. a "slightly faster speech right" or a "very much higher pitch average" as referenced in Table A, so that the presented adapted patron communication content would be recognized as being sentiment neutral using a mapping classification process as set forth in Table A.

Enterprise system 110 running augmentation process 113 can augment communication data for presentment to a patron user with non-neutral sentiment content. Various communication data for presentment to a patron user can be subject to content augmentation, including presented communication data presented by enterprise agent user 129 or communication data generated autonomously by an intelligent agent defined by enterprise system 110. Enterprise system 110 running augmentation process 113 can include enterprise system 110 using a decision data structure that cognitively maps exhibited sentiment by a patron user to action decision to return augmented content. Embodiments herein recognize that patron users exhibiting heightened sentiment can be induced to provide more accurate and more detailed information when their exhibited heightened sentiment is moderated. Accordingly, embodiments herein can provide augmented content to patron users in response to the patron users' exhibited sentiment for moderating sentiment exhibited by the patron users. Where sentiment moderation is performed autonomously by an intelligent agent, energies of a human enterprise agent user 129 are not consumed for purposes of sentiment moderation.

Augmented sentiment content presented to a patron user can include e.g. gesture content and/or spoken and/or written word content. In various embodiments an intelligent agent defined by enterprise system 110 can be capable of presenting sentiment moderating gestures to a patron user. For example, where an intelligent agent defined by enterprise system 110 controls a mechanical robot defining patron node interface 120 or the rendering of a 3D humanoid model representing a virtual agent, the intelligent agent can present gestures such as facial gestures or hand gestures to a patron user for moderation of a patron user's exhibited sentiment.

Enterprise system 110 running real time conference process 114 can include enterprise system 110 running various communication controls for support of real time audio and/or video data communications. Enterprise system 110 running real time conference process 114 can include enterprise system 110 supporting communications with patron node interface 120 and agent node interface 130 with use of the Real Time Transport Protocol (RTP) which is a network protocol for delivering audio and video over IP networks. RTP can run over user datagram protocol (UDP). RTP can be used in conjunction with RTP control protocol (RTCP). RTP can carry media streams, e.g. audio and video, and RTCP can be used to monitor transmission statistics and quality of service (QoS) which aides a facilitation of synchronization of multiple streams. RTP can be used to support voice over IP and can be used in connection with the signaling protocol such as the session initiation protocol (SIP) which establishes connections across a network. Aspects of the RTP are described in Request for Comments (RFC) 3550 published by the Internet Society (2003). Enterprise system 110 running real time conference process 114 can support a communication session provided by chat session in addition to or in place of supporting a communication session provided by a video conference session. For supporting a text-based chat session, enterprise system 110 can operate in accordance with internet relay chat protocol (IRCP) aspects of which are described in request for comments (RFC) 1459 updated by the following RFCs: 2810, 2811, 2812, 2813, and 7194. For support of a voice based chat session, enterprise system 110 can operate for example, according to the real time transport protocol (RTP) which is a network protocol for delivering audio and video over IP networks. Aspects of the RTP protocol are described in RFC 3550 as referenced hereinabove.

Enterprise system 110 running rendering process 115 can render a 3D model defining a virtual agent. System 100 can be configured according to one embodiment so that an intelligent agent (IA) defined by enterprise system 110 interacting with patron user 119 controls rendering of a 3D humanoid model to represent a humanoid virtual agent. In such an embodiment, patron node interface 120 can have corresponding rendering software so that patron node interface 120 can render an interactive 3D humanoid model representing a virtual agent. Enterprise system 110 running rendering process 115 can activate various gestures that can be acted by a virtual agent provided by a rendered 3D humanoid model. Gestures can include, e.g. rendered facial gestures and/or hand gestures. Rendered gestures can be in dependence on sentiment exhibited by a patron user.

Enterprise system 110 running robot control process 116 can run processes for control of a mechanical robot. System 100 can be configured according to one embodiment so that an intelligent agent defined by enterprise system 110 controls a mechanical robot which can have a physical instance at an enterprise venue such as a retail store or other enterprise venue wherein services are provided. According to one embodiment as set forth herein, patron node interface 120 can include a mechanical robot that can be controlled by enterprise system 110. Enterprise system 110 running robot control process 116 can include enterprise system 110 miming various gesture control processes such as facial gesture control processes and hand gesture control processes. The gesture control processes for controlling a mechanical robot can be in dependence on exhibited sentiment exhibited by patron user 119.

Figure 2:
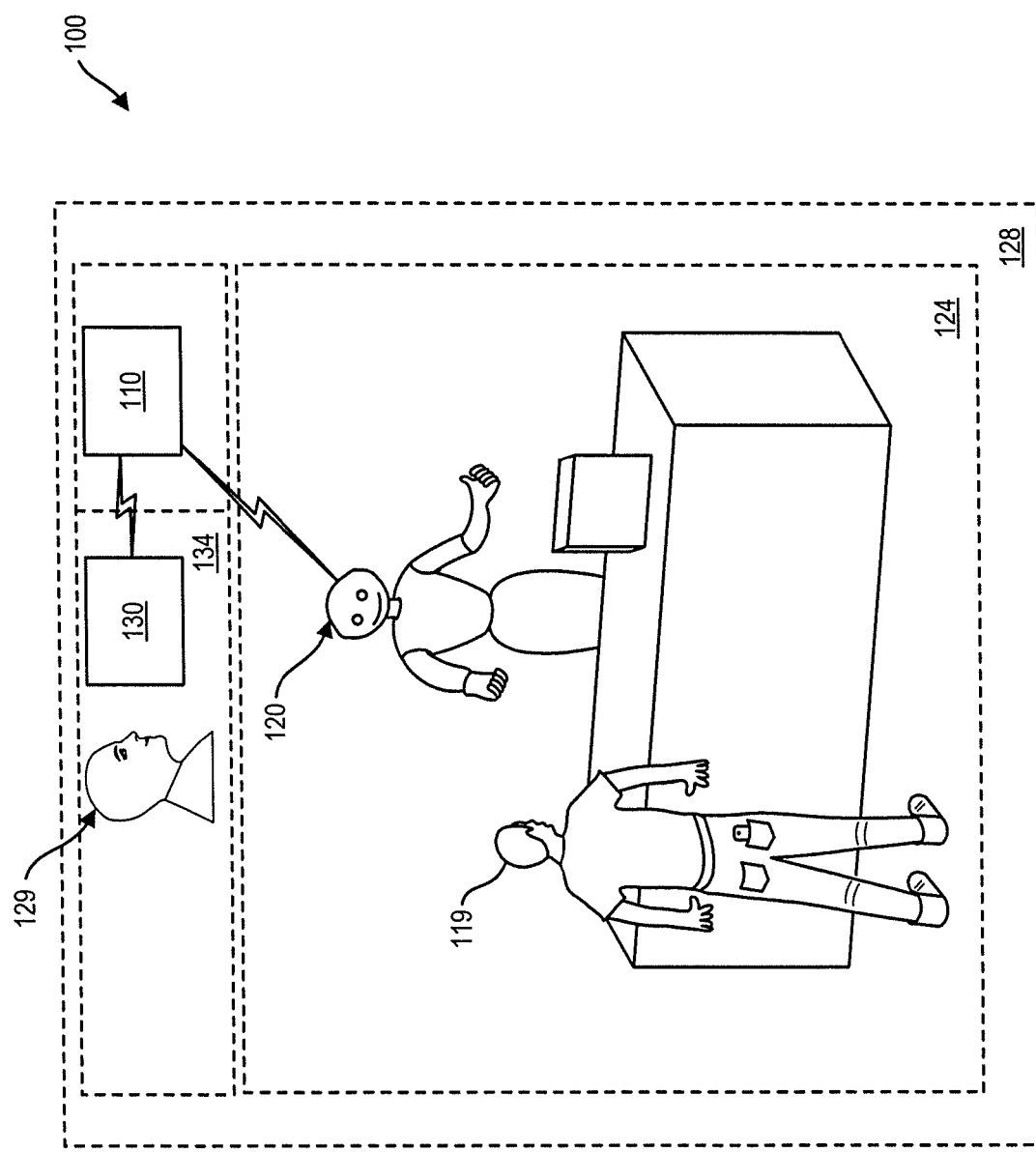
FIG. 2 is a physical and block schematic view of the system as shown in FIG. 1 according to one embodiment.
Figure 3:
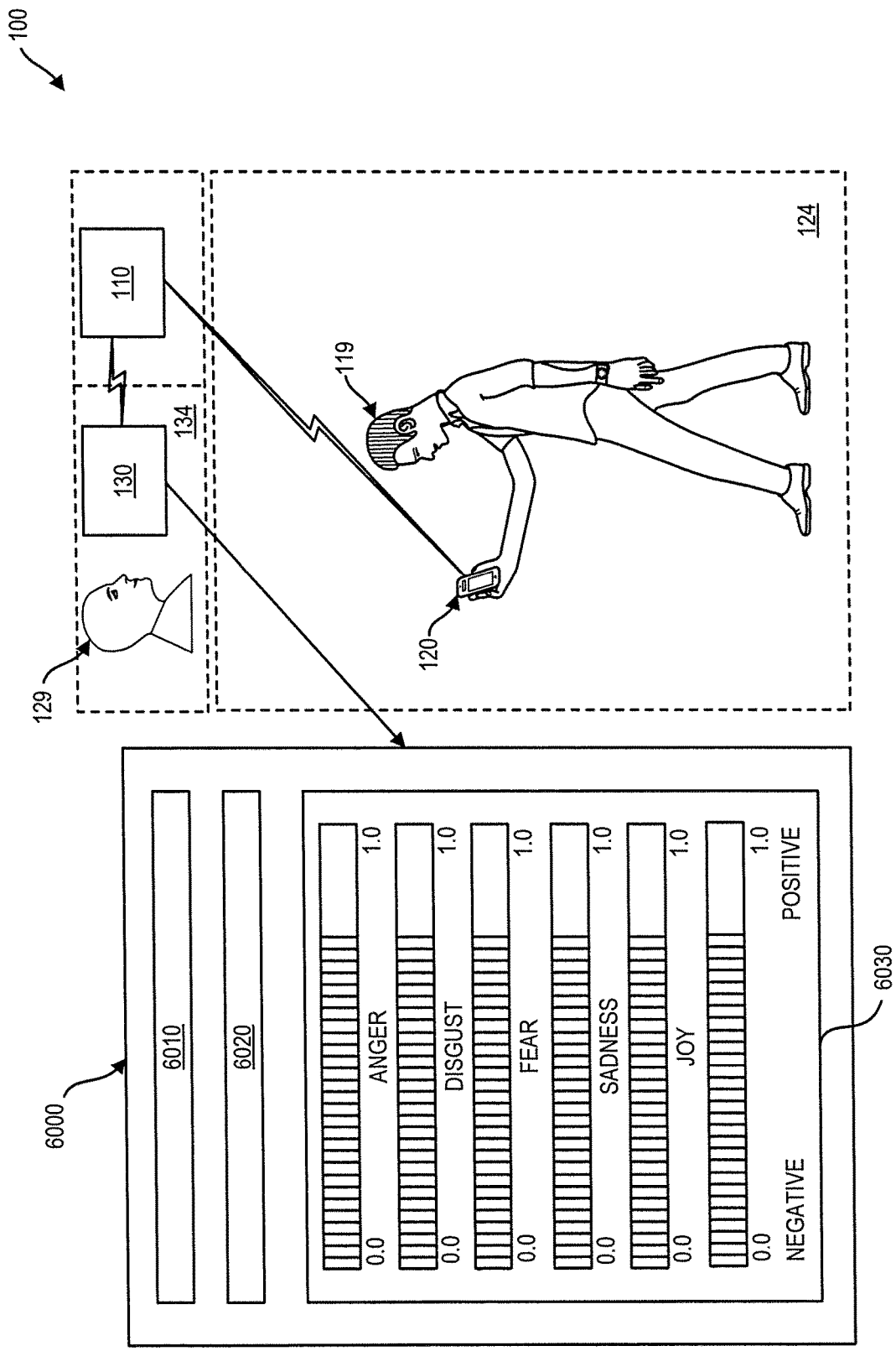
FIG. 3 is a physical and block schematic view of the system according to FIG. 1 according to one embodiment.

Various embodiments of a patron environment 124 are described in references to FIGS. 2 and 3. In the embodiment of FIG. 2, patron environment 124 can be provided by an enterprise venue, e.g. a retail store or a service enterprise. In the embodiment of FIG. 2, patron node interface 120 can include a mechanical robot under the control of an intelligent agent defined by enterprise system 110. In the patron environment depicted in FIG. 2, patron node interface 120 provided by a mechanical robot can be positioned, e.g. behind a physical patron user service counter and can be presenting communication content to patron user 119 based on adapted communication data sent to patron node interface 120 for presentment of communication content to patron user 119. The communication content can be presented in the form of, e.g. gesture communication content, synthesized voice communication content, and/or displayed text communication content which can be displayed on a display mounted to or otherwise associated to the mechanical robot defining patron node interface 120. In the embodiment of FIG. 2, patron environment 124 can be included in an enterprise venue 128, e.g. a retail store or another type of enterprise services venue. According to one embodiment, enterprise system 110 and agent node interface 130 can also be included in a common enterprise venue 128. In another embodiment patron node interface 120 provided by a mechanical robot and patron user 119 can be disposed in a common enterprise venue and one or more of enterprise system 110 or agent node interface 130 can be external and remote from enterprise venue 128.

In the embodiment of FIG. 3 patron environment 124 can include patron user 119 interacting with patron node interface 120, wherein patron node interface 120 is provided by a client computer device, e.g. a mobile client computer device such as a smartphone or another type of client computer device. Patron node interface 120 in the embodiment of FIG. 3 can present to patron user 119 communication content in the form of e.g. synthesized voice data and/or text data and/or gesture communication content defined by 3D model renderings of the humanoid model as/set forth herein. Enterprise system 110 can stream audio and/or video data and/or textual data to patron node interface 120 for presentment by patron node interface 120. According to one embodiment, enterprise system 110 as node can send data to patron node interface 120 for rendering an interactive 3D model on a display of patron node interface 120 so that there is rendered on patron node interface 120 a 3D model of a humanoid intelligent agent that is capable of rendered gestures in the form of, e.g. facial and/or hand gestures which can be rendered for display on a display of patron node interface 120.

Figure 4:
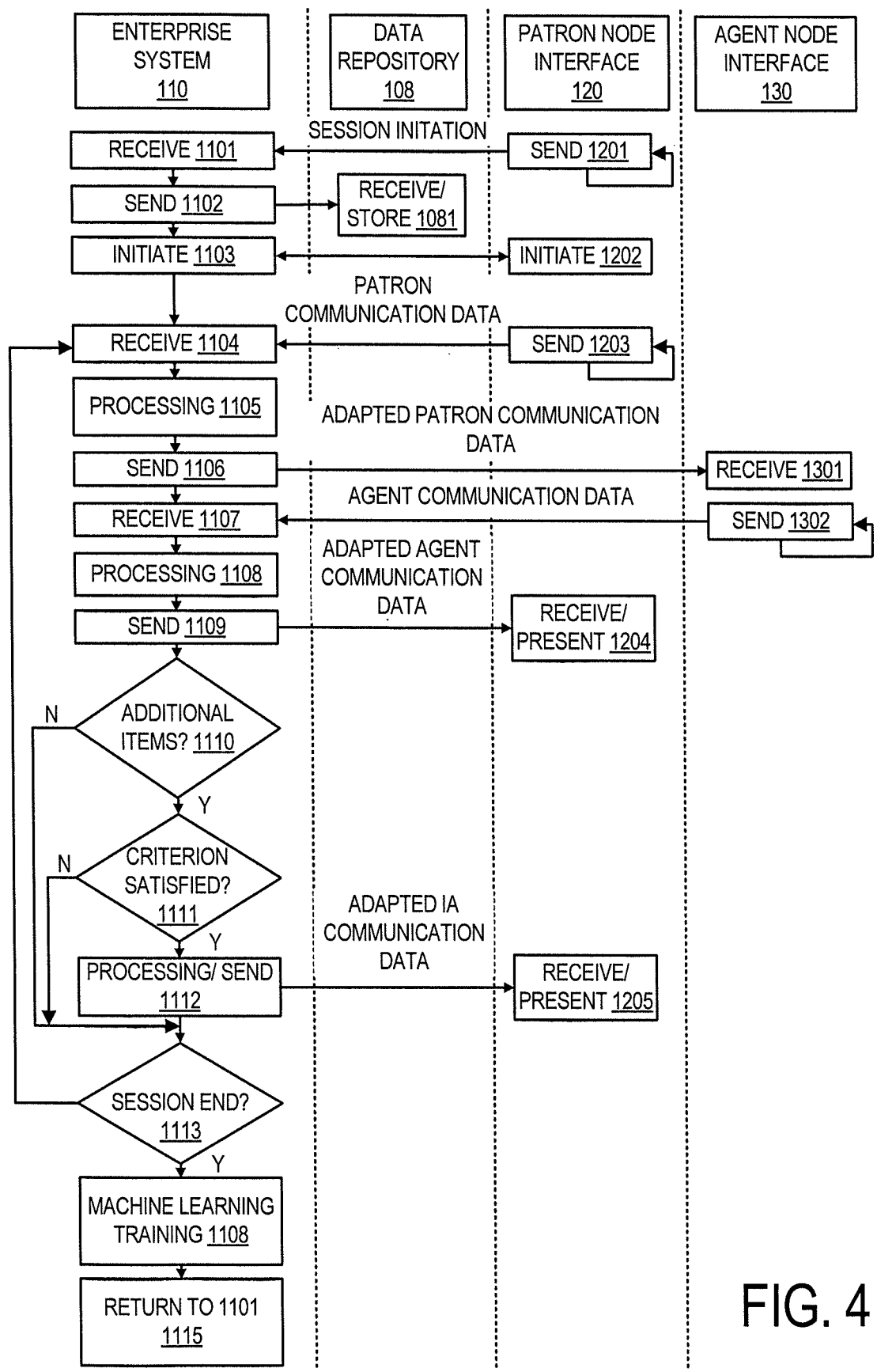
FIG. 4 is a flowchart illustrating a method for performance by an enterprise system interoperating with a patron node interface and an agent node interface according to one embodiment.

A method for performance by enterprise system 110 interoperating with patron node interface 120 and agent node interface 130 is set forth in reference to the flowchart of FIG. 4. At block 1101, enterprise system 110 can be receiving session initiation data from patron node interface 120 which can be sending session initiation data to enterprise system 110 at block 1201. In the case that patron node interface 120 is provided by a mechanical robot, the sending of session initiation data at block 1201 can include patron node interface 120 sending vocal utterance data of patron user 119 that can be picked up by an audio input device of patron node interface 120. In the case that patron node interface 120 is provided by a client computer device such as a mobile client computer device of a patron user, session initiation data sent by patron node interface 120 at block 1201 can include, e.g. login data transmitted through a web based user interface that can be displayed on a display of patron node interface 120. It will be understood that session initiation data can take on various forms. In response to receipt of session initiation data at block 1101, enterprise system 110 can proceed to block 1102.

At block 1102, enterprise system 110 can send session initiation data to data repository 108 for receipt and storage by data repository 108 at block 1081. At block 1102 performed by enterprise system 110 and block 1202 performed by patron node interface 120, enterprise system 110 and patron node interface 120 can perform appropriate handshaking to initiate a communication session between enterprise system 110 and patron node interface 120, which patron node interface 120 is being utilized by patron user 119.

At initiation block 1103, enterprise system 110 can have identified patron user 119 as a certain user, e.g. a registered user or a guest user of system 100. The identification can be based for example by a voice prompt defined by vocal utterance data of patron user and/or a user ID entered into a displayed user interface displayed on patron node interface 120. Performance of initiate blocks 1103 and 1202 can include for example initiation of a live video conference session and/or a live text based chat session. In response to completion of initiation block 1103, enterprise system 110 can proceed to block 1104.

At block 1104, enterprise system 110 can be receiving patron communication data from patron node interface 120. Patron node interface 120 can be sending patron communication data at block 1203. Patron communication data can be iteratively sent. Patron communication data sent at block 1203 can include, e.g. vocal utterance data and/or text based data entered by patron user 119 into a displayed user interface of patron node interface 120, and/or video data representing facial expressions of the patron user for example. In response to receiving patron communication data at block 1104, enterprise system 110 can proceed to block 1105.

At block 1105, enterprise system 110 can perform processing of received patron communication data. The processing at block 1105 can include processing to identify heightened sentiment content of patron communication data received at block 1104. Heightened sentiment content can include content having associated sentiment parameter values exceeding a threshold. According to one embodiment enterprise system 110 at processing block 1105 can activate sentiment analysis process 111 and sentiment reduction process 112 which utilizes sentiment analysis process 111.

Enterprise system 110 performing processing block 1105 can include enterprise system 110 returning sentiment parameter values for received sentiment communication data following sentiment parameter classifications: "anger", "disgust", "fear", "joy", and "sadness". In the case that patron communication data is received in the form of vocal utterance data, processing at block 1105 by enterprise system 110 can include activating a speech-to-text process to convert received vocal utterance data to text based data and then NLP processing can be performed on the returned text based data.

Processing at block 1105 by enterprise system 110 can include enterprise system 110 processing received vocal utterance data to return sentiment parameter values across the sentiment parameters "anger", "disgust", "fear", "joy", and "sadness" using a vocal utterance acoustic characteristic mapping process as described in reference to Table A.

Processing at block 1105 by enterprise system 110 can include enterprise system 110 processing received vocal utterance data to return sentiment parameter values across the sentiment parameters "anger", "disgust", "fear", "joy", and "sadness" using video data processing to recognize facial expressions and using the recognized facial expressions for return of the sentiment parameter values.

Accordingly, at block 1105 returned sentiment parameter values can be returned using a plurality of alternative sentiment analysis processes. Where common content is associated to sentiment parameter values returned using alternative processes, multiple values returned by alternative processes can be aggregated, e.g. subject to averaging, identifying a median value, making a weighted average, averaging with filtering, or other processes to return an aggregated result. With sentiment parameter values returned at block 1105, enterprise system 110 at block 1105 can return adapted patron communication data corresponding to the patron communication data received at block 1104. The adapted patron communication data can include enterprise system 110 returning sentiment reduced patron communication data having reduced sentiment parameter values relative to original patron communication data received at block 1104.

Enterprise system 110 performing processing at block 1105 can include enterprise system 110 according to one embodiment performing sentence segmentation processing to identify, e.g. phrases and words within sentences. At block 1105 enterprise system 110 can examine returned sentiment parameter values and can identify sentiment parameter values exceeding a threshold, e.g. a phrase having an anger parameter value of >0.7, a phrase having a disgust parameter value of >0.7, a phrase having a fear parameter value of >0.7, a phrase having a joy parameter value of >0.7, or a phrase having a sadness parameter value of >0.7. Where enterprise system 110 identifies a phrase having one or more sentiment parameter value exceeding a threshold, enterprise system 110 can provide a sentiment reduced sentence having the phrase so that a meaning of the sentence having the phrase is maintained but the adapted segment has an associated sentiment parameter value reduced relative to the value associated to the original content.

For performing communication data processing at block 1108 enterprise system 110 can process one or more segment of communication data that has been segmented using one or more segmentation process. Communication data can be segmented by one or more of e.g. pauses in vocal utterance data, sentences, phrases, words, and the like.

Figure 5:
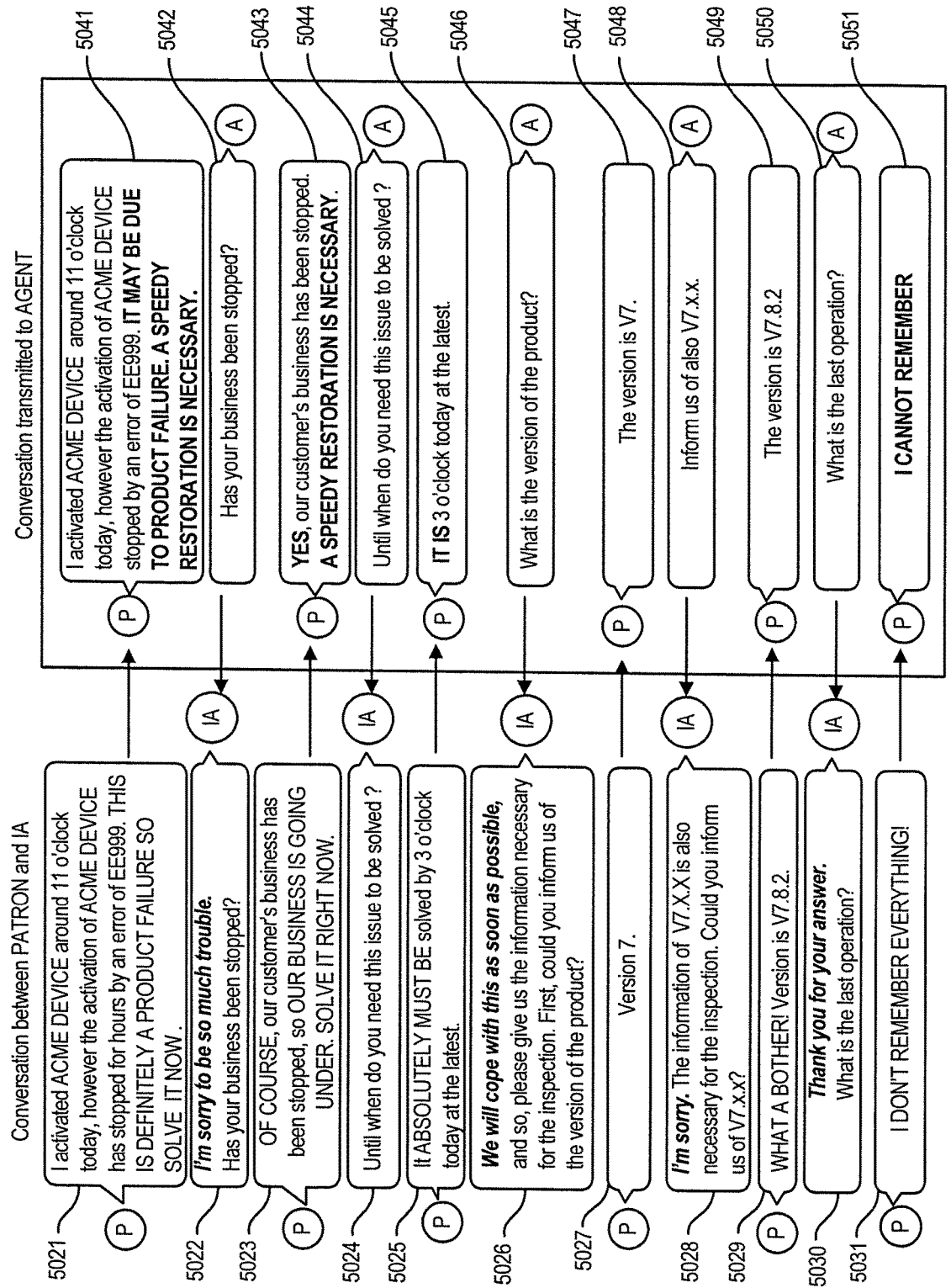
FIG. 5 is a schematic diagram illustrating sentiment reduction processes and sentiment augmentation processes that can be performed by an enterprise system according to one embodiment.

Enterprise system 110 performing processing of received patron communication data for return of adapted sentiment reduced patron communication data is described further in reference to FIG. 5. On the left hand side of FIG. 5 there is indicated in the boxes labeled "P" original communication data content received from a patron user. The original communication data content on the left hand side of FIG. 5 can be, e.g. text converted from vocal utterance data entered by a patron user into patron user interface 130 or original text based content entered into a user interface of patron node interface 120 by a patron user.

On the right hand side of FIG. 5 in the boxes labeled "P", there is depicted sentiment reduced communication data content adapted from the originally presented patron user communication data. The adapted patron communication data shown in the boxes labeled "P" on the right hand side of FIG. 5 can be sentiment neutral communication data that is sentiment reduced relative to the originally presented content of a patron user on the left hand side of FIG. 5.

While the right side content is sentiment reduced relative to the left side patron content of FIG. 5, the meaning of the original content is preserved. Embodiments herein recognize that enterprise agents can better focus on concerns of patron users when their energies are focused on communicated factual items of the patron user rather than on efforts to moderate exhibited sentiment of a patron user.

Accordingly, as set forth herein enterprise system 110 can return adapted patron communication data that is sentiment reduced relative to originally presented patron data communication. The sentiment reduced content can be sent to an enterprise agent and thus can be in a form adapted for more efficient and more accurate response by an enterprise agent user. An enterprise agent user can more accurately enter factual items of communication data into a computer system, for example, with energies of the agent users not consumed by moderating an emotional state of a patron user. Adapted sentiment reduced patron communication data sent to an agent user can be sentiment neutral, e.g. can have sentiment parameter values below threshold values indicative of a neutral sentiment. For example, the returned adapted sentiment reduced communication data can include segments of communication data wherein the communication data is absent of phrases or other content segments having associated "anger", "disgust", "fear", "joy", and "sadness" sentiment parameter values exceeding 0.3, for example.

Enterprise system 110 can present a communication by the sending of the adapted patron communication data sent at block 1106. In response to receipt of the communication data sent at block 1106 and received by agent node interface 130 at block 130, agent node interface can display the communication data to define text based communication content. In response to receipt of the communication data sent at block 1106 and received by agent node interface 130 at block 130, agent node interface can in addition or alternatively playback the communication data by way of audible voice synthesis to define synthesized voice based communication content.

Figure 6:
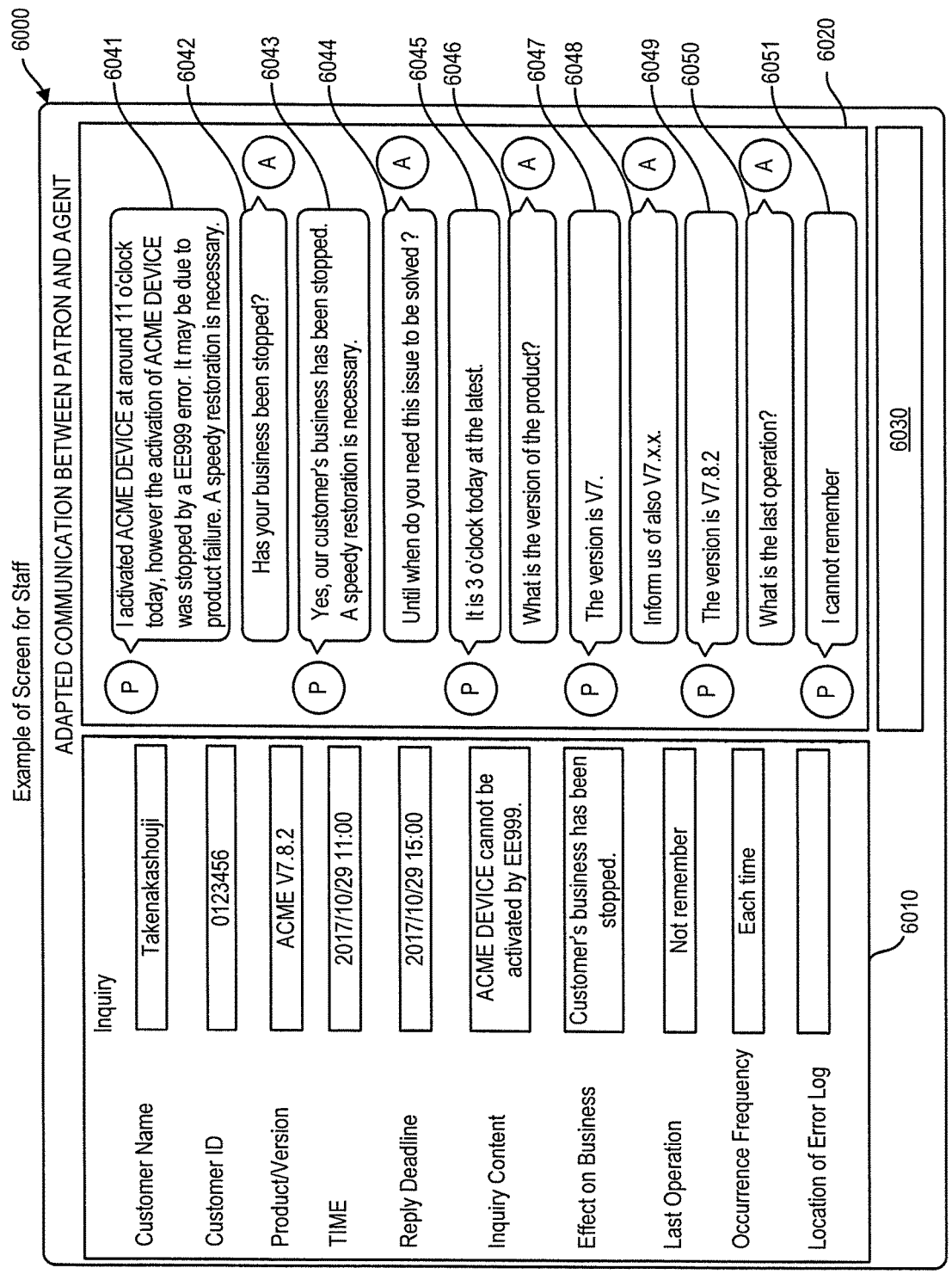
FIG. 6 depicts a user interface for display on a displayed user interface of an enterprise agent user according to one embodiment.

FIG. 6 depicts a user interface 6000 which can be a displayed user interface for display on a display of a client computer device defining agent node interface 130 according to one example. User interface 6000 as shown in FIG. 6 can guide an agent user to complete a list of factual data items based on a communication session with a patron user. On the left side of FIG. 6 there can be presented a data field list of factual items required for completion based on a communication session with a patron user. The factual items can be factual items, for example, to register an IT support ticket. In area 6010 of user interface 6000 a list of form data items can be displayed which need to be completed. Area 6010 graphically presents to an enterprise agent user data items that have been received and data items which still need to be obtained that are indicated by open data fields for example. Enterprise system 110 can use part of speech tagging to identify factual data items that satisfy open field items specified in area 6010. Enterprise system 110 running an NLP process can return part of speech flags that identify nouns mapping to entity topics that can include entity topics satisfying required items of a requirements form list described with reference to area 6010.

On the right side of user interface 6000 there can be displayed in area 6012 of user interface 6000 text based data specifying content of a current communication session between a patron user and an enterprise agent.

According to system 100 a communication session between a patron user 119 and an enterprise agent user 129 can be mediated by an intelligent agent defined by enterprise system 110, e.g. so that enterprise system 110 subjects received communication data from a patron user to sentiment reduction so that sentiment reduced and sentiment neutral content defining adapted communication data is sent to an enterprise agent user 129.

Referring to FIG. 6, right side text boxes of user interface 6000 can display in area 6020 adapted communication data subject to sentiment reduction of heightened sentiment content removed from the adapted communication data that is displayed on user interface 6000 an enterprise agent user 129 can better focus on factual items communicated within communication data and therefore is better able to accurately facilitate the completion of form data using a form as depicted in area 6010, leading to more accurate data entry, reduced data errors, and improved computer system utilization.

With a need for reentries of data reduced, system 100 can yield improved computer system resource utilization advantages. For return of reduced sentiment patron communication data, enterprise system 110 can according to one embodiment use various predictive models. Predictive models can be used to predict the meaning of an identified phrase that has been identified by enterprise system 110 at processing block 1105. Enterprise system 110 for return of sentiment reduced communication data at block 1105 can use predictive models that have been trained with training data to predict a sentiment neutral meaning of certain phrases that have been identified as heightened sentiment phrases.

Referring to user interface 6000, user interface 6000 in area 6030 can display an emotion graph with graphs indicating sentiment parameter values for one or more sentiment parameter. The graph indicated sentiment parameter values can be the current (most recently determined) sentiment parameter values for the patron user. Viewing area 6030, an enterprise agent user can observe the exhibited sentiment of a patron user in a detached manner without observing the original communication from the patron user. FIG. 3 depicts an emotion graph presented in area 6030 according to one embodiment, which emotion graph can be presented with a form list in area 6010 for indicating factual data items for collection, and in area 6020 indicating data of current adapted communication session between an patron user and an enterprise agent user.

Figure 7:
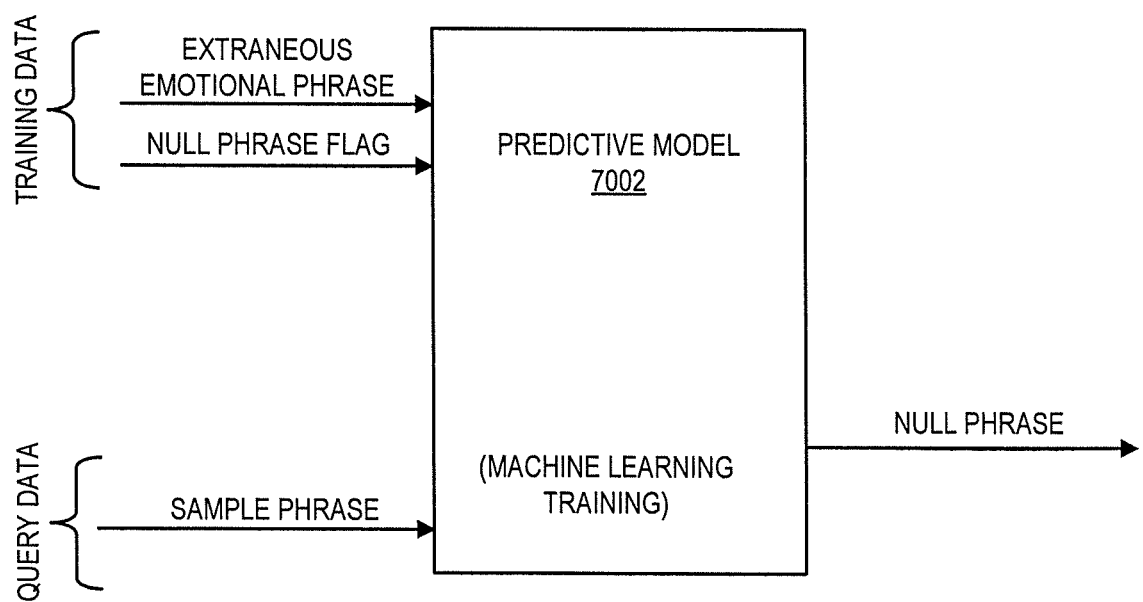
FIG. 7 depicts a predictive model that can be trained for return of predictions for use by an enterprise system according to one embodiment.

FIG. 7 depicts a predictive model 7002 for predicting that an identified emotional phrase has a "null" meaning, i.e. does not have a discernable meaning and that a larger content segment with the phrase has a common meaning in the absence of the extraneous phrase. An emotional phrase herein can be regarded to be a phrase having a sentiment parameter value in one or more of the five sentiment parameters "anger", "disgust", "fear", "joy", and/or "sadness" exceeding a defined threshold. Predictive model 7002 as set forth in FIG. 7, once trained using supervised machine learning training processes, is able to predict that an input sample phrase is a "null" phrase. With use of predictive model 7002, when predictive model 7002 predicts that an input sample phrase is a "null" phrase, can adapt a current content segment by removing the sample phrase from the sample content segment. For training of predictive model 7002, predictive model 7002 can have applied thereto iterative sets of training data. Each set of training data can include a selected emotional phrase in combination with a "null" phrase flag for that selected emotional phrase. Selected extraneous emotional phrases for training of predictive model 7002 can be selected by an enterprise agent user 129 by observation of actual data accumulated over time by system 100 by patrons. In different enterprise environments extraneous emotional phrases having "null" meaning can be expected to be differentiated. Sets of training data for training of predictive model 7002 can include for example the following training datasets: (a) "What a bother!"; meaning=null; (b) "Your organization is incompetent!"; meaning=null; (c) "I'm never using ACME again!"; meaning=null; (d) "Our business is going under!"; meaning=null; and so on. With training data applied as described, predictive model 7002 can learn emotional phrases that are merely extraneous and have a null meaning and therefore can be safely removed for providing adapted communication data without changing a factual meaning of input communication data received from a patron user. In some cases, predictive model 7002 for predicting that an entered emotional phrase can be trained with training data in which emotional phrases known in the field of the relevant enterprise to define exaggerations are applied as training data.

Figure 8:
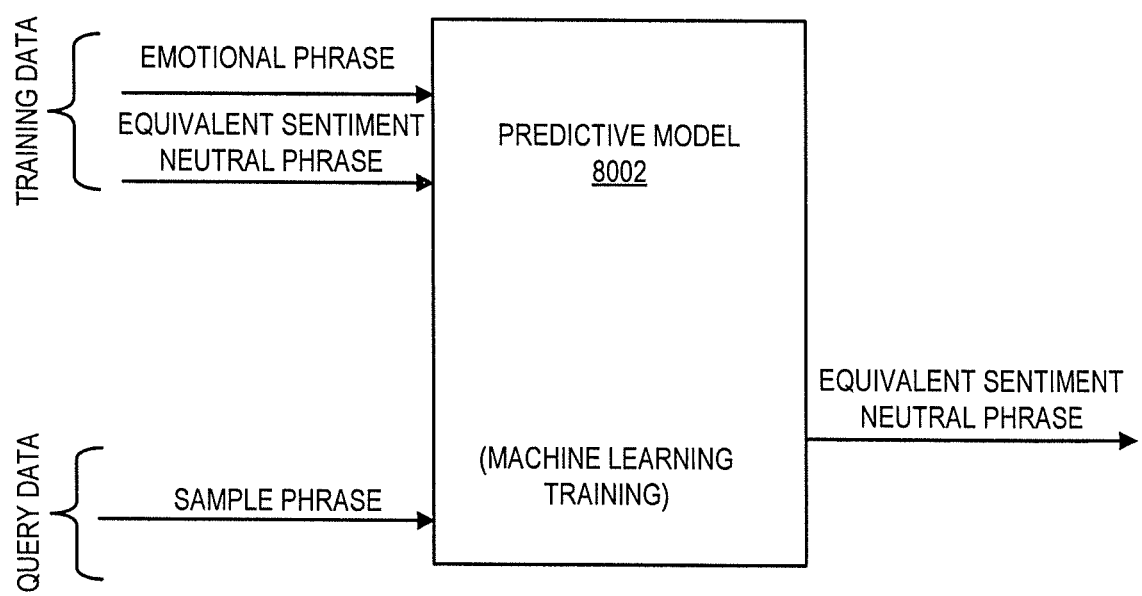
FIG. 8 depicts a predictive model that can be trained by machine learning processes for use for return of predictions by an enterprise system according to one embodiment.

Predictive model 8002 as shown in FIG. 8 can predict that an identified emotional phrase has an equivalent meaning to a certain specified sentiment neutral phrase. For training of predictive model 8002 as shown in FIG. 8, an administrator user for example can observe accumulated data of historical communication sessions between patron users and an enterprise agent and can identify phrases special to an endeavor of an enterprise as having a meaning in common with a certain sentiment neutral phrase. Predictive model 8002 can be trained with use of supervised machine learning training processes. Predictive model 8002 can be trained with use of iteratively applied sets of training data. Respective iteratively applied training data can include, for example, a specified emotional phrase in combination with a specified equivalent sentiment neutral phrase, e.g. as identified by an administrator user of an enterprise as having a sentiment neutral meaning in common with the emotional phrase. Training data for training predictive model 8002 can include iteratively applied training data sets as follows: (s) "Solve it now!"; meaning="a speedy restoration is necessary"; (b) "Solve it right now!"; meaning="a speedy restoration is necessary"; (c) "This needs to be fixed yesterday!"; meaning="a speedy restoration is necessary"; (d) "Get this fixed now!"; meaning="a speeding restoration is necessary"; and so on. It will be seen that predictive model 8002 can be trained using machine learning processes that certain emotional phrases have meanings in common with certain specified equivalent sentiment neutral phrases. Prior to input of a specified sentiment neutral phrase as applied training data for training predictive model 8002, a designated sentiment neutral phrase can be subject to NLP processing to confirm that the sentiment neutral phrase actually returns sentiment parameter values that are sentiment neutral, e.g. below a threshold. Predictive model 8002 can be trained to return a plurality of different equivalent sentiment neutral phrases in dependence on input sample data. Predictive model 8002 once trained by machine learning is capable of responding to query data to return an equivalent sentiment neutral phrase.

In response to a sample phrase input into predictive model 8002, which sample phrase can be an emotional phrase having one or more heightened sentiment parameter value, can return an equivalent sentiment neutral phrase. The equivalent sentiment neutral phrase can have meaning in common with the input sample phrase but can have one or more sentiment parameter value reduced relative to the one or more sentiment parameter value of the sample phrase and further the output equivalent sentiment neutral phrase can be absent of any sentiment neutral parameter exceeding a specified threshold.

Use of predictive model 7002 for deletion of an emotional phrase from original patron communication data and/or use of predictive model 8002 for return of a sentiment neutral equivalent phrase that is equivalent in meaning to an input emotional phrase of original patron communication data can provide adapted patron communication data that is adapted for use in consumption by an enterprise agent by having one or more sentiment parameter value associated to the adapted communication data reduced relative to a value associated to the original patron communication data.

Referring to FIGS. 5 and 6, phrases on the left side of FIG. 5 flagged as being emotional phrases are indicated in capital letters. Referring to FIG. 5, it is seen that the adapted patron communication data of the right side of FIG. 5 has changes relative to the original patron communication data of the left side of FIG. 5. For example, referring to boxes 5021 and 5041 the phrase "This is definitely a product failure" is adapted and represented as "IT MAY BE DUE TO A PRODUCT FAILURE". Further with reference to boxes 5021 and 5041 of FIG. 5, the phrase "Solve it now, right now!" is adapted and represented as "A SPEEDY RESTORATION IS NECESSARY." Referring to boxes 5023 and 5043, the phrase "Solve it right now!" is adapted and represented (on the right side of FIG. 5) as "A SPEEDY RESTORATION IS NECESSARY" (box 5043). The phrase "I don't remember everything!" of box 5031 is adapted and represented as the sentiment neutral phrase "I CANNOT REMEMBER IT".

In some cases phrases, e.g. based on use of predictive model 7002, are recognized as being extraneous emotional phrases and are removed altogether by the processing performed by enterprise system 110. For example, referring to boxes 5029 and 5049 the phrase "What a bother!" is adapted and represented so that the phrase "What a bother!" is removed altogether from the corresponding adapted communication segment that is presented to the enterprise agent user (see box 5049). With further reference to the flowchart of FIG. 4, enterprise system 110 on completion of processing block 1105 can proceed to block 1106.

At block 1106, enterprise system 110 can send adapted patron communication data for receipt by agent node interface 130 at block 1301. In response to the receipt of the agent node of the adapted patron communication data at block 1301, agent node interface 130 can display a received adapted communication data as indicated by user interface 6000 of FIG. 6, wherein adapted communication data of a patron can be displayed in text based boxes 6041-6051. Enterprise system 110 can present a communication by the sending of the adapted patron communication data sent at block 1106. In response to receipt of the communication data sent at block 1106 and received by agent node interface 130 at block 130, agent node interface can display the communication data to define text based communication content. In response to receipt of the communication data sent at block 1106 and received by agent node interface 130 at block 130, agent node interface can in addition or alternatively play-back the communication data by way of audible voice synthesis to define synthesized voice communication content.

In response to received adapted communication data received at block 1301, an agent user can enter into agent node interface 130 responsive data, e.g. using a text based interface and/or using a voice based interface. Agent communication data of an agent entered by an agent can be sent at block 1302 for receipt by enterprise system 110 at block 1107. In response to the receipt of agent communication data at block 1107 enterprise system 110 can proceed to block 1108.

At block 11108, enterprise system 110 can perform processing of received agent communication data. According to one embodiment, agent communication data with reference to user interface 6000 can be missing form data observable from area 6010. For example, an agent user can observe missing items as may be indicated by empty data fields of area 6010 and may enter agent communication data, e.g. textually or with vocal utterances to request that a patron user provide the missing factual item data. Enterprise system 110 performing processing of received agent communication data at block 1108, based on received agent communication data received at block 1107 can include enterprise system 110 activating augmentation process 113 described in reference to FIG. 1.

Enterprise system 110 performing augmentation process 113 can include enterprise system 110 adding content to agent communication data received at block 1107 in dependence on an exhibited sentiment exhibited by a patron user. The exhibited sentiment exhibited by a patron user can according to one embodiment, be a most recently exhibited sentiment of a patron user. Enterprise system 110 performing block 1108 can include enterprise system 110 using a decision data structure stored in decision data structures area 2124. An example decision data structure for use by enterprise system 110 in performing processing at block 1108 is set forth in Table B.

TABLE B

| Row | Most Recent Patron Sentiment | Gesture Action Decision | VA Speech Action Decision |
|---|---|---|---|
| 1 | Anger > 0.7 | Apologetic gesture(s) | Apologetic phrase(s) |
| 2 | Joy > 0.7 | Joyful gesture(s) | Joyful phrase(s) |
| 3 | Sadness > 0.7 | Comforting gesture(s) | Comforting phrase(s) |
| ... | ... | ... | ... |

Referring to the decision data structure of Table B, the decision data structure of Table B cognitively maps an exhibited sentiment exhibited by a patron user to one or more action decision. The action decisions can include, e.g. gesture action decisions and/or intelligent agent speech action decisions. Action decisions specified in the decision data structure of Table B can be in dependence on a most recently exhibited patron sentiment. In the case that a patron user has determined to have most recently exhibited an "anger" sentiment parameter value exceeding a threshold, e.g. of 0.7 the gesture action decision and intelligent agent speech action decision of Row 1 can be fired. In the case that a determined most recently exhibited patron sentiment is a "joy" sentiment parameter value exceeding a threshold, e.g. 0.7 the gesture action decision and intelligent agent speech action decision of Row 2 can be fired. In the case that a most recently exhibited sentiment of a patron user is a "sadness" sentiment parameter value exceeding a threshold, e.g. 0.7 the action decisions of Row 3 specified in Table B can be fired. Gesture action decisions can be returned in embodiments wherein patron node interface 120 is capable of presenting observable gestures to a patron user 119. Such use cases can include use cases wherein patron node interface 120 includes a mechanical robot as depicted in FIG. 2 or where patron node interface 120 displays a rendering of a rendered humanoid model of an intelligent agent.

Referring to the decision data structure of Table B where a most recently exhibited patron sentiment is an "anger" sentiment parameter value exceeding a threshold, returned gesture action decisions can specify the return of apologetic gesture(s) and returned intelligent agent speech action decisions can include the return of apologetic phrase(s) defined by synthesized voice phrases and/or text based phrases. Embodiments herein recognize that responding to a patron user exhibiting a heightened "anger" sentiment with apologetic gesture(s) and or spoken phrase(s) may reduce an exhibited anger sentiment of a patron user to thereby improve the factual data item content of data received from the patron user. An example of an apologetic facial gesture can include, e.g. lowering of the head and examples of an apologetic hand gestures can include, e.g. opening hands toward a patron user or holding a hand over the heart area of a mechanical robot or humanoid rendered intelligent agent. Examples of apologetic speech phrases can include "I'm sorry", "we are sorry", "we are so sorry for the inconvenience", and the like.

Referring to Row 2 of the decision data structure of Table B, "joyful" gestures can include, e.g. laughing and/or smiling gestures, joyful hand gestures can include, e.g. the hand gesture of raising the hands way up or the thumbs up signs, and examples of joyful phrases can include, e.g. "hooray", "that's great", "congratulations!", and the like. Referring to Row 3 of the decision data structure of Table B, an example of a comforting facial expression gesture can include, e.g. nodding of the head, e.g. of a mechanical robot or of a rendered 3D humanoid model of an intelligent agent, an example of a comforting hand gesture can include, e.g. briefly clasping the hands together by a mechanical robot or a rendered 3D humanoid intelligent agent, and an example of a comforting speech phrase can be the phrase "we will cope with this as soon as possible" and the like. On completion of processing at block 1108, enterprise system 110 can proceed to block 1109.

At block 1109 enterprise system 110 can send adapted agent communication data for receipt by patron node interface 120 at block 1204. At block 1204, patron node interface 120 can respond to the received adapted agent communication data sent by enterprise system 110 to present a communication to the patron user 119. The adapted agent communication data can include one or more gesture communication data or speech communication data. Presentment of received gesture communication data can include acting out of the gesture by a mechanical robot or by a rendered 3D humanoid model of an intelligent agent. Presentment of received adapted agent communication data in the form of speech data can include, e.g. synthesized voice production of the adapted agent communication data and/or text based production of the received adapted agent communication data received at block 1204. In response to completion of block 1109, enterprise system 110 can proceed to block 1110.

Enterprise system 110 can present a communication by the sending of the adapted enterprise agent communication data sent at block 1109. In response to receipt of the communication data sent at block 1109 and received by patron node interface 120 at block 1204, patron node interface 120 can present an observable gesture to define non-verbal gesture communication content either via mechanical robot control or virtual model rendering. In response to receipt of the communication data sent at block 1109 and received by patron node interface 120 at block 1204, patron node interface 120 can play back the communication data to define synthesized voice communication content. In response to receipt of the communication data sent at block 1109 and received by patron node interface 120 at block 1204, patron node interface 120 can display the communication data to define text-based communication content.

At block 1110 enterprise system 110 can determine whether there are additional factual data items to collect from the user, e.g. as specified in a form indicated in area 6010 of user interface 6000 as shown in FIG. 6. Enterprise system 110 at block 1110 can determine whether there are additional factual data items from a user to collect that have been listed on an item information form stored in forms area 2122 as set forth herein. According to one example, a form for completion according to one example can be a form for initiation of an IT ticket. In the case that there are additional items to collect, enterprise system 110 can proceed to block 1111 to determine whether one or more criterion has been satisfied.

The one or more criterion evaluated at block 1111 can be one or more criterion to determine whether communication data is to be generated for automatic sending to a patron user. With reference to the user interface 6000 of FIG. 6, system 100 can be configured so that enterprise system 110, e.g. in forms area 2122 stores a list of automated questions to a patron user that are mapped to each data field listed in area 6010. For example, the data field "patron user name" can have a mapped question of "What is your name?", the data field "patron user ID" can have a mapped question of "What is your patron user ID?", and so on. The mapped questions mapped to data fields of area 6010 can have a baseline form stored in forms area 2122. The baseline form of the baseline questions can be sentiment neutral, e.g. can be absent of content having sentiment parameter values exceeding the threshold of, e.g. 0.3 for sentiment parameters such as "anger", "disgust", "fear", "joy", and "sadness".

One or more criterion evaluated at block 1111 by enterprise system 110 can include timeout criterion. For example, enterprise system 110 can be configured so that mapped predetermined sentiment neutral questions can be selected in dependence on a timeout criterion being satisfied. For example, enterprise system 110 can be configured to wait for an agent user to specify a question for collection of factual information from a patron user but if the enterprise agent user does not specify the question prior to a timeout period, enterprise system 110 automatically generates the mapped predetermined question corresponding to a form field by reading the question from the described predetermined list of mapped questions mapped to data fields of a form as described in connection with area 6010 of user interface 6000. On the condition that one or more criterion for sending such predetermined questions generated by enterprise system 110 from a mapped predetermined list mapping to data fields of a form can be regarded to be intelligent agent generated questions, given that in the described scenario, system 100, enterprise system 110 acts as an intermediary intelligent agent mediating communications between patron user 119 and enterprise agent user 129 as shown in FIG. 1. The described intelligent agent defined by enterprise system 110 can, for example, augment enterprise agent entered content as specified in FIG. 5, wherein augmentations provided by an intelligent agent defined by enterprise system 110 are indicated by boxes labeled with the label "IA" for intelligent agent.

Referring to FIG. 5, the content labeled with the indicator "A" can be content provided by a human enterprise agent user according to one embodiment, but in some embodiment, the content indicated by "A" can include or be content provided by an intelligent agent herein e.g. in response to one or more criterion being satisfied.

Further in reference to FIG. 5, content entered by an enterprise agent user 129 are labeled in FIG. 5 with the label A for agent, i.e. enterprise agent. With further reference to the flowchart of FIG. 4, enterprise system 110 on the determination that one or more criterion for sending intelligent agent generating communication data in the form of question data to a patron user are satisfied, enterprise system 110 can proceed to block 1112.

At block 1112, enterprise system 110 can perform processing to adapt autonomously generated intelligent agent communication data for sending to a patron user. The processing by enterprise system 110 at block 1112 can be in common with the processing of enterprise system 110 performed at block 1108 to determine augmented sentiment content for augmenting communication data except that at block 1112 autonomously generated intelligent agent generated question data can be subject to augmenting rather than agent generated question data subject to augmenting at block 1108.

Processing at block 1112 can include activating augmentation process 113 as described in connection with FIG. 1. At block 1112, enterprise system 110 can perform processing to augment baseline question data that has been mapped to factual data entry fields specified in reference to area 6010 of user interface 6000. Enterprise system 110 performing processing at block 1112 to augment intelligent agent generated question data can include performing augmenting in dependence on an exhibited sentiment exhibited by a patron user. The exhibited sentiment can be, e.g. the most recently exhibited sentiment of the patron user. Enterprise system 110 performing processing at block 1112 can include enterprise system 110 performing content augmentation with use of a decision data structure as set forth in Table B in the manner described with reference to processing block 1108. For example, with reference again to Table B, the Row 1 gesture and VA speech action decisions can be fired when the Row 1 condition is satisfied, the Row 2 gesture and VA speech action decisions can be fired when the Row 2 condition is satisfied, and the Row 3 gesture and VA speech action decisions can be fired when the Row 3 condition is satisfied. Accordingly, at block 1112 action decisions can be returned to associate to generated communication data generated by an intelligent agent defined by enterprise system 110 to associated to communication data one or more of an associated gesture(s) and one or more of an associated phrase(s), set forth in reference previously to processing block 1108 and the decision data structure of Table B.

Enterprise system 110 can present a communication by the sending of the adapted enterprise agent communication data sent at block 1112. In response to receipt of the communication data sent at block 1112 and received by patron node interface 120 at block 1205, patron node interface 120 can present an observable gesture to define nonverbal gesture communication content either via mechanical robot control or virtual model rendering. In response to receipt of the communication data sent at block 1109 and received by patron node interface 120 at block 1204, patron node interface 120 can play back the communication data to define synthesized voice communication content. In response to receipt of the communication data sent at block 1109 and received by patron node interface 120 at block 1204, patron node interface 120 can display the communication data to define text based communication content.

Referring again to block 1110, enterprise system 110 on the determination that no additional factual items are needed from a patron user can proceed to block 1113 to determine whether a current communication session has ended. Enterprise system 110 can also proceed to block 1113 when decision block 1111 returns the decision that one or more criterion for sending intelligent agent generated communication data are not satisfied and enterprise system 110 can also proceed to block 1113 on completion of block 1112.

Enterprise system 110 at block 1112 can send the described adapted intelligent agent communication data for receipt and presentment by patron node interface 120 at block 1205. The receipt and presentment of adapted intelligent agent communication data at block 1205 can be in the manner of the receipt and presentment of the adapted enterprise agent communication data received and presented at block 1204, e.g. received and presented communication data can include one or more of an accompanied gesture(s), one or more synthesized voice content, and/or text based content. Enterprise system 110 on completion of block 1112 can proceed to block 1113.

At block 1113, enterprise system 110 can determine whether a current communication session between a patron user and an enterprise agent user as mediated by enterprise system 110 has ended. In the case that a communication session has not ended, enterprise system 110 can return to block 1104 and can iteratively perform blocks 1104-1113 iteratively until enterprise system 110 at block 1113 determines that a communication session between a patron user and an enterprise agent has ended. On completion of block 1113 enterprise system 110 can proceed to block 1114.

At block 1114, enterprise system 110 can perform machine learning training processing. For example, predictive models such as predictive models 7002 and 8002 can be subject to reinforcement learning machine learning training based on data indicating an observed success or failure of the just completed communication session. Success or failure criterion can include such criterion as whether all factual information of a form were collected and/or the speed of completion of the communication session and the like. In the case that the preceding communication session was scored with a performance score exceeding a threshold, the utilized predictive models can be subject to reinforcement training, e.g. which can result in increased reported confidence levels associated to returned predictions. In the case a preceding section was subject to a score below a performance threshold, predictive model is utilized during the preceding session can be subject to negative reinforcement machine learning training which can result in, e.g. reduced confidence levels associated to return predictions returned with use of predicted models utilized during a preceding communication session. Thus, over time with use of machine learning training the performing predictive models can be utilized for performance of predictions during a communication session between a patron user and an enterprise agent user intermediated by enterprise system 110.

Enterprise system 110 at machine learning training block 1114 can also parse out and present in a separate list phrases identified during a preceding communication session between a patron user and an enterprise agent user that have been identified by enterprise system 110 as being emotional phrases having one or more sentiment parameter values above a defined threshold. An administrator user can selectively use such separated emotional phrases special to the endeavor of a specific enterprise for subsequent machine learning training of predictive models for use in returning predictions or in some embodiments such separated emotional phrases separated by enterprise system 110 can be automatically applied by enterprise system 110 as training data of training datasets for training of predictive models for use in subsequent communication sessions between a patron user and an enterprise agent. Enterprise system 110 on completion of block 1114 can proceed to block 1115. Enterprise system 110 at machine learning training block 1114 can add voice samples to an area of users area 2121 defining voice profile for a particular user so that a corpus of training data supporting the voice profile is augmented.

Various available tools, libraries, and/or services can be utilized for implementation of predictive model 7002 and predictive model 8002. For example, a machine learning service can provide access to libraries and executable code for support of machine learning functions. A machine learning service can provide access set of REST APIs that can be called from any programming language and that permit the integration of predictive analytics into any application. Enabled REST APIs can provide e.g. retrieval of metadata for a given predictive model, deployment of models and management of deployed models, online deployment, scoring, batch deployment, stream deployment, monitoring and retraining deployed models. According to one possible implementation, a machine learning service provided by IBM® WATSON® can provide access to libraries of APACHE® SPARK® and IBM® SPSS® (IBM® WATSON® and SPSS® are registered trademarks of International Business Machines Corporation and APACHE® and SPARK® are registered trademarks of the Apache Software Foundation. A machine learning service provided by IBM® WATSON® can provide access set of REST APIs that can be called from any programming language and that permit the integration of predictive analytics into any application. Enabled REST APIs can provide e.g. retrieval of metadata for a given predictive model, deployment of models and management of deployed models, online deployment, scoring, batch deployment, stream deployment, monitoring and retraining deployed models. Training predictive model 6002 can include use of e.g. support vector machines (SVM), Bayesian networks, neural networks and/or other machine learning technologies.

At block 1115, enterprise system 110 can return to block 1101 to receive session initiation data from patron node interface 120. Embodiments herein recognize that enterprise system 110 can be mediating a plurality of communication sessions between enterprise system 110 and a plurality of instances of patron node interface 120 concurrently and simultaneously.

Embodiments herein recognize that in various embodiments such as in remote support centers for middleware products, technical support engineers may endeavor to resolve the patron's software problem via phone, without going on site. Various software products such as middleware products can have a high business impact. Embodiment herein recognize that patrons calling or otherwise interacting with a support center exhibit heightened sentiment which can be identified in various ways e.g. by determining that an exhibited anger sentiment parameter value has exceeded a threshold. Embodiments herein recognize that enterprise agent users such as support engineers tend to focus too much on easing his anger, instead of gathering the technical information needed for the problem resolution. Even after hanging up the phone, enterprise agent users may have trouble to release this mental pressure due to the patron user's angry voice. Accordingly, it is difficult for enterprise agent users to concentrate on the problem investigation, which is the most important tasks for them.

According to one embodiment, an intelligent agent (IA) can be interposed between a patron user and an enterprise agent user support engineer to remove the negative impact of the patron user's angry feelings. The intelligent agent can change the severe tone of the patron user into a flat tone, and transmits only the necessary technical content for problem investigation to the support engineer so that the patron user's anger doesn't negatively affect the support engineer. The intelligent agent (AI) can change the normal tone of the enterprise agent user into an apologetic tone, and transmits both the technical content and the apologized sentence to the patron user. Example: Patron user "I activated ACME DEVICE around 11 o'clock today, however the activation of ACME DEVICE has stopped for hours by an error of EE999. This is definitely a product failure so solve it now. Right now."

Intelligent agent (IA): "I activated ACME DEVICE around 11 o'clock today, however the activation of ACME DEVICE has stopped by an error of EE999. It may be due to product failure. A speedy restoration is necessary."

The enterprise agent user may then author (e.g. via vocal utterance or typed text): "Send us SystemOut.log of ACME DEVICE". The IA may then adapt the enterprise agent user's response as follows: "We are very sorry for the inconvenience. We will do our best to resolve this issue as soon as possible. Could you provide us SystemOut.log of ACME DEVICE?"

The patron user can make an inquiry to the support center by communication means including a voice communication function, for example, through a video calling (internet connection) from a patron user's terminal such as a telephone (voice line) or a smartphone. Alternatively or additionally the patron user can interact with a mechanical robot controlled by the IA e.g. at an enterprise venue is physical proximity with the patron user.

The intelligent agent can receive the inquiry, and can perform a voice recognition process. The intelligent agent can perform various processes to recognize a patron user e.g. can examine an entered patron user ID entered by a patron user and/or perform facial recognition using received video data representing the patron user or use another biological data recognition process. In these processes, the intelligent agent can return sentiment attribute data in the form of sentiment parameter values associated to received communication data of the patron user, wherein the communication data can include e.g. one or more of vocal utterance data, entered text data entered by a patron user, or video data representing the patron user.

The intelligent agent can extract factual content including factual data items from the received communication data. The intelligent agent for return of factual content can use e.g. part of speech tagging to identify nouns that specify factual data items of a predetermined list.

An intelligent agent can process factual content of received communication data until filling items of a predetermined list (filling "slots (blanks)" as an AI term), while the intelligent agent can automatically generate additional questions as needed. In addition to or alternatively to an intelligent agent generating questions, an enterprise agent can present questions.

Returned sentiment attribute data can be stored in a data repository.

The content of a communication session and the content of a requirements form list can be iteratively streamed to a user interface for display on a client computer device of an enterprise agent user's client computer device.

The enterprise agent user can grasp the situation while watching the filled requirements. When the enterprise agent user needs information other than the standard form list requirements for replying to the inquiry content, the enterprise agent user can input, e.g. via vocal utterance or in text, an additional one or more question that is sent to the patron user through the intelligent agent.

The response input by the staff can be presented to the patron user, according to one embodiment, after being appropriately changed into an emotion-rich response (sentiment addition) depending on the state of the patron user's exhibited sentiment in accordance with the sentiment attribute data saved in the data repository.

An intelligent agent (IA) can recognizes patron user's exhibited sentiment, from the condition of the voice obtained from the communication means, the facial expression during the video calling, other biological information obtained from the terminal, entered text entered by the patron user and the like. Then, the intelligent agent converses with the patron user, depending on the recognized exhibited sentiment. For example, the intelligent agent converses with an apologetic tone in the case of a wrathful tone (e.g. indicated by an anger sentiment parameter value exceeding a threshold), converses with a joyful tone in the case of a joyful tone (e.g. indicated by a joy sentiment parameter value exceeding a threshold), and converses with a comforting tone in the case of a sad tone (e.g. indicated by a sadness sentiment parameter value exceeding a threshold).

Further, the intelligent agent can remove heightened sentiment content from the words of the patron user, and can relay (streaming) the resulting flat phrase to the staff. At the time of the first call, the intelligent agent deals without the interposition of the staff, until the necessary information is obtained. On this occasion, when the patron user demands something unreasonable, for example, "Correct a description error in the manual by tomorrow", the intelligent agent explains to the human enterprise agent user, for example, "The correction of the description error in the manual has a low urgency level and requires a month", in accordance with the support rule.

Thereby, the staff can use, for the inspection, the time taken to cope with the patron user's emotion conventionally and the time taken to get the requirements conventionally, resulting in an early resolution of the patron user's problem, efficient and accurate data entry to a computer system and efficient computer resource utilization. The intelligent agent can indicate the recognized patron user's exhibited sentiment as an emotion graph, and the staff can optionally display the emotion graph at a lower portion of the screen, to grasp the patron user's emotion.

In addition to the case of a trouble about which the patron user is angry, the present invention can be applied to the case where the patron user joyfully calls the support center for talking to someone and the intelligent agent recognizes the gleeful speaking manner and converses with the patron user sympathetically. Also in this case, the staff on the backend side can grasp the situation through the emotion graph, and can deal coolly and objectively. An example of an augmented conversation in which there is positive sentiment exhibited by a user is as follows.

Patron user: "We newly purchased a product called ACME DEVICE recently. We want to operate many functions. What convenience will we obtain by using this product?"

Intelligent agent: "Thank you for purchasing our ACME DEVICE. We will support you as much as possible, such that ACME DEVICE will be helpful to your business."

Support staff "ACME DEVICE enhances security."

Intelligent agent: "The most useful function of ACME DEVICE is to enhance security. This is a very excellent function."

According to one embodiment, communication data of a patron user can be processed. According to one example, a conversation between a patron user and an enterprise agent user intermediated by an intelligent agent can be as follows.

Patron user (with vocal utterance): "Of course, our patron user's business has been stopped, so our business is going under. Solve it right now." Voice waveform data can be processed (+biological data that can be acquired and used by smartphone and the like) such as voice inflection and voice intensity (defining vocal utterance acoustical characteristics as set forth herein).

Intelligent agent: separate the input data into state indicating emotion and context (factual content), for return of sentiment neutral communication data. (Example) emotion state: anger=0.8, context (factual content): patron's business stopped, expedited restoration is needed; sentiment neutral communication data "Yes, our patron user's business has been stopped. A speedy restoration is necessary."

Certain embodiments herein may offer various technical computing advantages involving computing advantages to address problems arising in the realm of computer systems and computer networks. Embodiments herein recognize that a fundamental aspect of the operation of computer systems is in respect to their interactions with users and embodiments herein can remove heightened sentiment content associated with entry of factual data items into a computer system for improved accuracy of entered information data items and for improved efficiency of data operation with reduced computer system resource utilization associated, e.g. with recapture of mis-entered or unentered data, extended communication sessions, missed data items, and the like. Embodiments herein can feature an enterprise system defining intelligent agent that can mediate communications between a patron user and an enterprise agent user. Embodiments herein can feature reduction of expressed values of sentiment associated with input data for return of a sentiment neutral communication data for sending to an enterprise agent user so that the enterprise agent user's attention can be on the facilitation of unencumbered use of a computer system for accurate capture of data without use of human energies for the management and moderation of sentiment exhibited by a patron user. Embodiments herein can feature use of a process generated intelligent agent performing automated processes with use of artificial intelligence (AI) action decisions to automatically manage and moderate exhibited sentiment of a patron user for more accurate and efficient capture of factual information items from a patron user. Embodiments herein can feature a mechanical robot that receives communication data from a user and runs automated AI processes, for example, to moderate exhibited sentiment of a patron user. Embodiments herein can feature a intelligent agent having synthesized voice capabilities, text presentment capabilities, rendered 3D humanoid model capabilities, and in some cases a mechanical robot presence running AI processes for return of action decisions that can moderate exhibited sentiment of a patron user. Embodiments herein can feature use of multiple different sentiment analysis processes for return of sentiment parameter values. Sentiment analysis processing can include e.g. processes to examine acoustical characteristics of vocal utterances, Natural Language Processing (NLP) processes and processes to examine video data representing sentiment indicating facial expressions. Various decision data structures can be used to drive artificial intelligence (AI) decision making, such as decision data structure that cognitively maps exhibited sentiment attributes to action decisions specifying attributes of return communications to a patron user. Decision data structures as set forth herein can be updated by machine learning so that accuracy and reliability is iteratively improved over time without resource consuming rules intensive processing. Machine learning processes can be performed for increased accuracy and for reduction of reliance on rules based criteria and thus reduced computational overhead. For enhancement of computational accuracies, embodiments can feature computational platforms existing only in the realm of computer networks such as artificial intelligence platforms, and machine learning platforms. Embodiments herein can employ data structuring processes, e.g. processing for transforming unstructured data into a form optimized for computerized processing. Embodiments herein can examine data from diverse data sources such as e.g. audio input devices, video input devices and keypads for text entry. Embodiments herein can include artificial intelligence processing platforms featuring improved processes to transform unstructured data into structured form permitting computer based analytics and decision making. Embodiments herein can include particular arrangements for both collecting rich data into a data repository and additional particular arrangements for updating such data and for use of that data to drive artificial intelligence decision making. Certain embodiments may be implemented by use of a cloud platform/data center in various types including a Software-as-a-Service (SaaS), Platform-as-a-Service (PaaS), Database-as-a-Service (DBaaS), and combinations thereof based on types of subscription.

Figure 9:
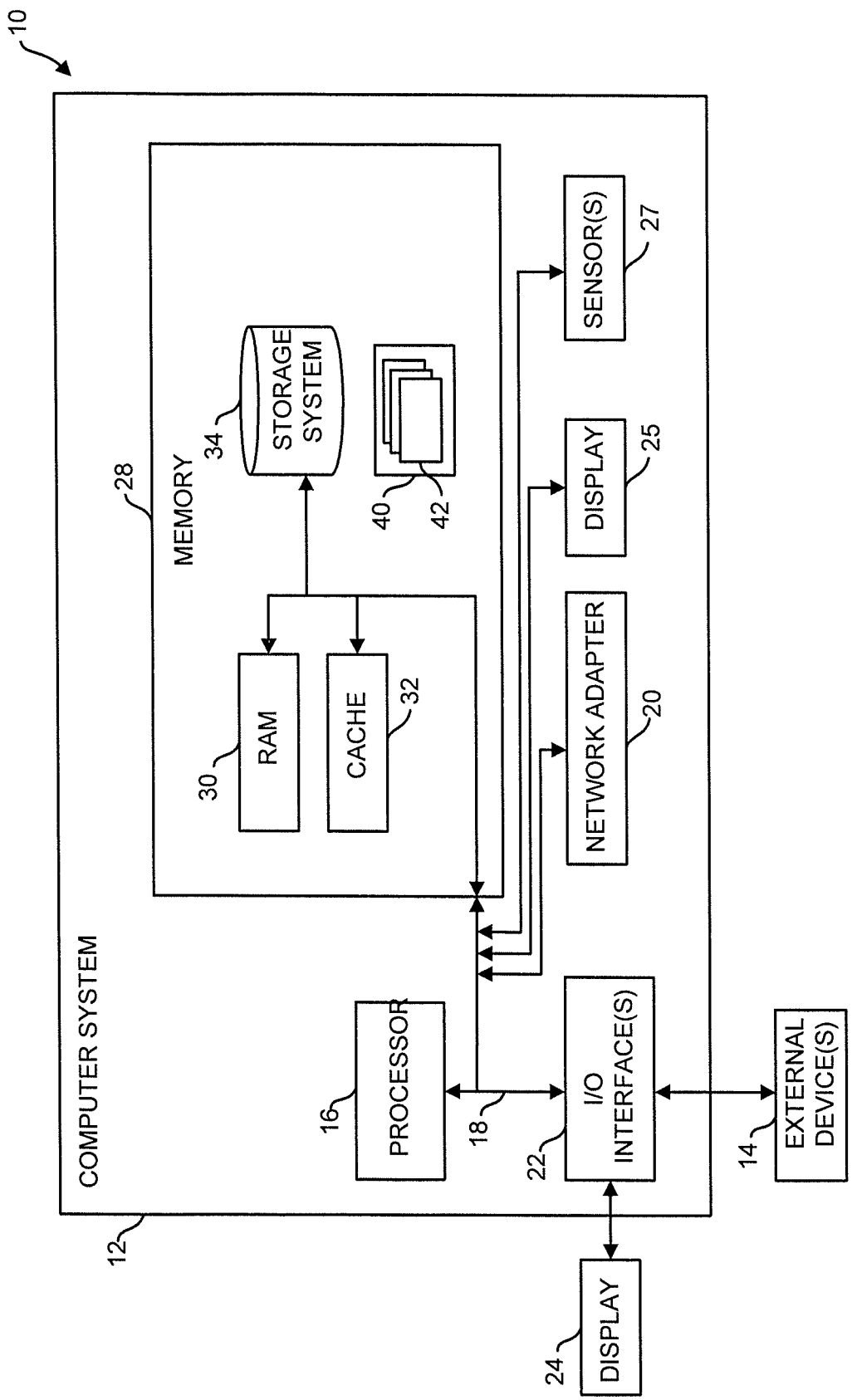
FIG. 9 depicts a computing node according to one embodiment.
Figure 10:
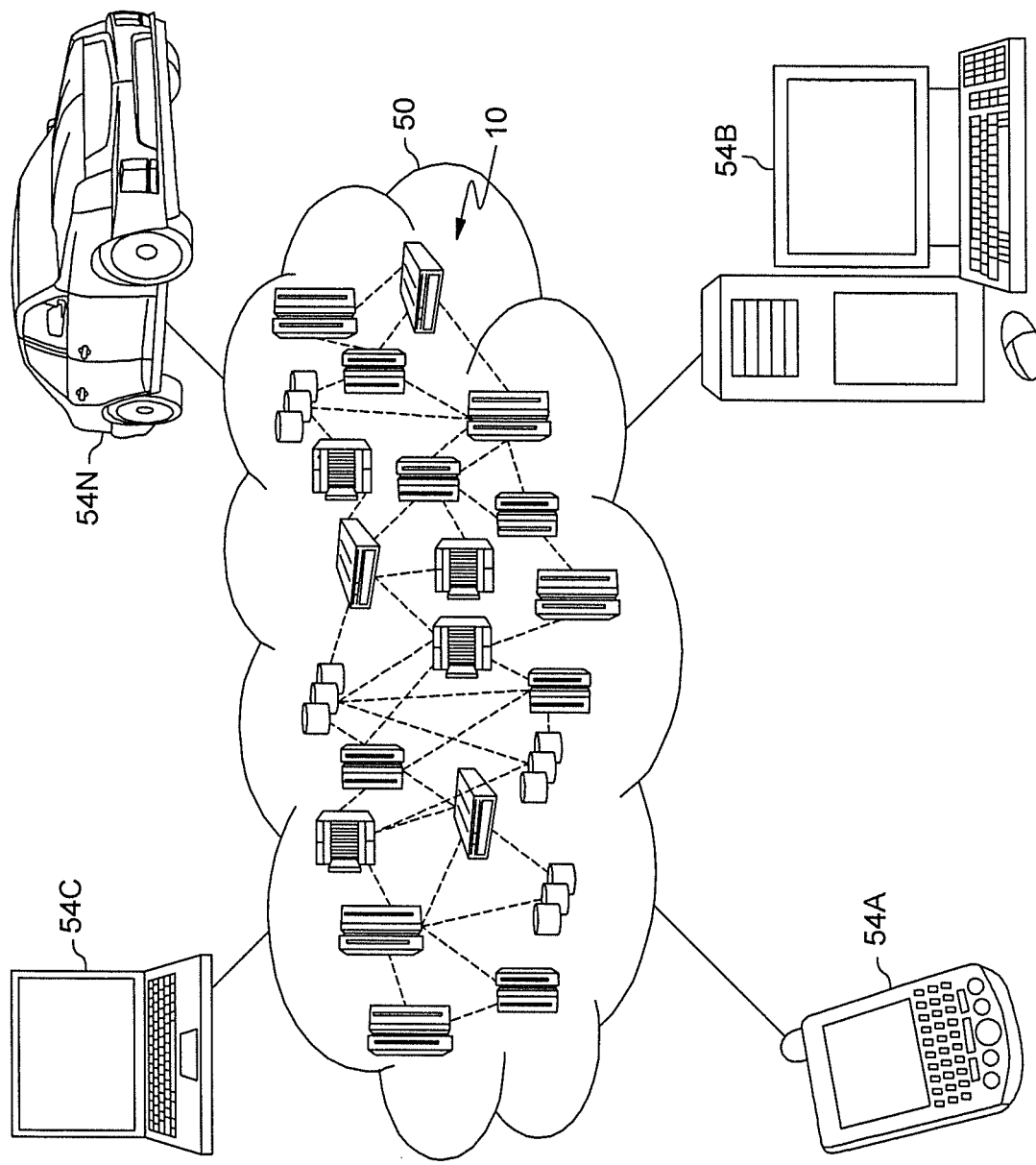
FIG. 10 depicts a cloud computing environment according to one embodiment.
Figure 11:
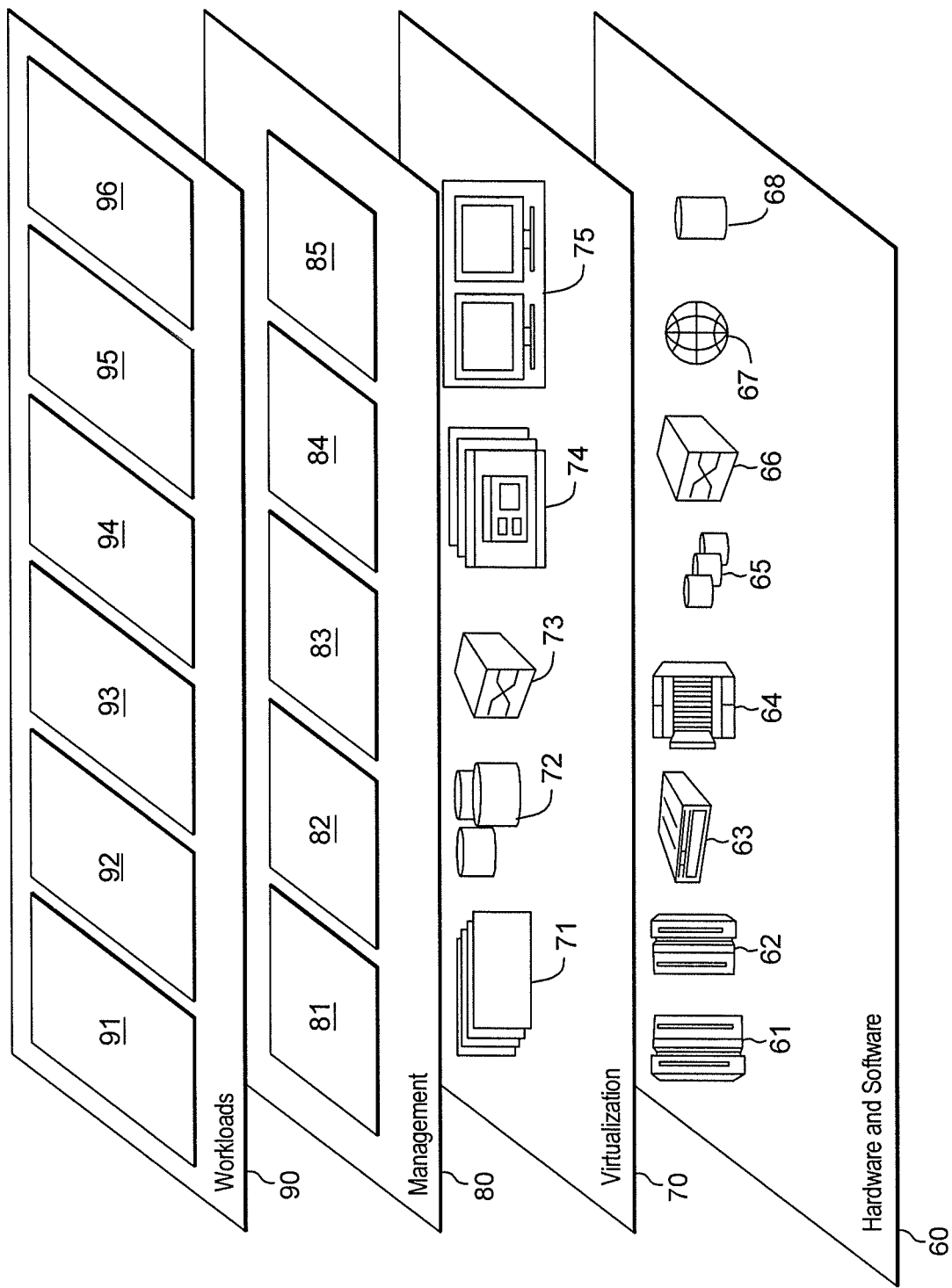
FIG. 11 depicts abstraction model layers according to one embodiment.

FIGS. 9-11 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 9, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 9, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 10-11.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. In one embodiment, enterprise system 110 can include one or more computing node 10 and can include one or more program 40 for performing functions described with reference to enterprise system 110 as set forth in the flowchart of FIG. 4. In one embodiment, patron node interface 120 can include one or more computing node 10 and can include one or more program 40 for performing functions described with reference to patron node interface 120 as set forth in the flowchart of FIG. 4. In one embodiment, agent node interface 130 can include one or more computing node 10 and can include one or more program 40 for performing functions described with reference to agent node interface 130 as set forth in the flowchart of FIG. 4. In one embodiment, the computing node based systems and devices depicted in FIGS. 1-3 can include one or more program for performing function described with reference to such computing node based systems and devices.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch screen display and can be configured to provide user interface functionality, e.g. can facilitate virtual keyboard functionality and input of total data. Computer system 12 in one embodiment can also include one or more sensor device 27 connected to bus 18. One or more sensor device 27 can alternatively be connected through I/O interface(s) 22. One or more sensor device 27 can include a Global Positioning Sensor (GPS) device in one embodiment and can be configured to provide a location of computing node 10. In one embodiment, one or more sensor device 27 can alternatively or in addition include, e.g., one or more of a camera, a gyroscope, a temperature sensor, a humidity sensor, a pulse sensor, a blood pressure (bp) sensor or an audio input device. Computer system 12 can include one or more network adapter 20. In FIG. 10 computing node 10 is described as being implemented in a cloud computing environment and accordingly is referred to as a cloud computing node in the context of FIG. 10.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for adapting communications as set forth herein. The processing components 96 can be implemented with use of one or more program 40 described in FIG. 9.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements but is not limited to possessing only those one or more steps or elements. Likewise, a step of a method or an element of a device that "comprises," "has," "includes," or "contains" one or more features possesses those one or more features but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method comprising:
examining communication data of a first human user to return one or more sentiment attribute of the communication data;
processing the communication data to return sentiment neutral adapted communication data, the processing being in dependence on the one or more sentiment attribute;
presenting to a second human user a sentiment neutral adapted communication, the sentiment neutral adapted communication being based on the sentiment neutral adapted communication data;
augmenting second communication data to return adapted second communication data, the augmenting being in dependence on the one or more sentiment attribute; and
presenting to the first human user an adapted second communication, the adapted second communication being based on the adapted second communication data.

2. The computer implemented method of claim 1, wherein the second communication data is communication data of the second human user.

3. The computer implemented method of claim 1, wherein the second communication data is an autonomously generated predetermined question that maps to an open field of a form list of open factual data items for collecting from the first human user, the form list being displayed on user interface viewable by the second human user.

4. The computer implemented method of claim 1, wherein the presenting the adapted second communication data includes using a mechanical robot physically located in an environment of the first human user.

5. The computer implemented method of claim 1, wherein the examining communication data of the first human user includes one or more of the following selected from the group consisting of: (a) examining converted vocal utterance data of the first human user converted to text using a speech to text converter; (b) examining acoustical characteristics of vocal utterance data of the first human user to return sentiment data based on a mapping between vocal utterance acoustical characteristics and exhibited sentiment; (c) examining text based data entered into a client computer device by the first human user; and (d) examining video data representing facial expressions of the first human user.

6. The computer implemented method of claim 1, wherein the processing the communication data to return sentiment neutral adapted communication data includes identifying a certain phrase defined by the communication data having a sentiment parameter value exceeding a threshold, predicting that the certain phrase has a null meaning and replacing the certain phrase with a null phrase.

7. The computer implemented method of claim 1, wherein the processing the communication data to return sentiment neutral adapted communication data includes identifying a certain phrase defined by the communication data having a sentiment parameter value exceeding a threshold, predicting that the certain phrase has a meaning in common with a particular sentiment neutral phrase and replacing the certain phrase with the particular sentiment neutral phrase.

8. The computer implemented method of claim 1, wherein the presenting to the first human user the adapted second communication includes presenting to the first human user one or more of the following selected from the group consisting of: (a) a facial expression gesture by a mechanical robot; (b) a hand gesture by a mechanical robot; (c) a facial expression gesture by a rendered 3D humanoid model representing a virtual agent; (d) a hand gesture by a rendered 3D humanoid model representing a virtual agent; (e) a synthesized voice communication, and (f) a text communication.

9. The computer implemented method of claim 1, wherein the presenting to a second human user a sentiment neutral adapted communication includes presenting a communication including each of: (a) a synthesized voice communication, and (b) a text communication, and wherein the presenting to the first human user the adapted second communication includes presenting to the first human user each of: (i) a facial gesture; (ii) a hand gesture; (iii) a synthesized voice communication, and (iv) a text communication.

10. The computer implemented method of claim 1, wherein the augmenting the second communication data to return adapted second communication data includes using a decision data structure that cognitively maps exhibited sentiment of the first human user to action decisions specifying communication content augmentations.

11. The computer implemented method of claim 1, wherein the communication data of a first human user to return one or more sentiment attribute of the communication data, includes identifying a phrase defined by the communication data, determining that the phrase has a sentiment parameter value exceeding a threshold, wherein the sentiment parameter value is an anger sentiment parameter value.

12. The computer implemented method of claim 1, wherein the adapted communication data has an associated anger sentiment parameter value that is reduced relative to an anger sentiment parameter value associated to the communication data.

13. The computer implemented method of claim 1, wherein the adapted communication data has an associated anger sentiment parameter value that is reduced relative to an anger sentiment parameter value associated to the communication data, and wherein the communication data is a communication data segment representing one or more of the following selected from the group consisting of: (a) a vocal utterance segment delimited by a pause; (b) a sentence; (c) a phrase, (d) a word.

14. The computer implemented method of claim 1, wherein the second communication data is communication data of the second human user, wherein the processing the communication data to return sentiment neutral adapted communication data includes identifying a certain phrase defined by the communication data having a sentiment parameter value exceeding a threshold, and replacing the certain phrase with an alternative phrase.

15. The computer implemented method of claim 1, wherein the second communication data is communication data received from the second human user, and wherein the augmenting second communication data to return adapted second communication data includes adding one or more phrase to the second communication data.

16. The computer implemented method of claim 1, wherein the processing the communication data to return sentiment neutral adapted communication data includes identifying a certain phrase defined by the communication data having a sentiment parameter value exceeding a threshold, predicting that the certain phrase has a meaning in common with a particular alternative phrase and replacing the certain phrase with the particular alternative phrase.

17. The computer implemented method of claim 1, wherein the examining communication data of a first human user to return one or more sentiment attribute of the communication data includes examining communication data received from the first human user to return one or more sentiment attribute of the communication data, wherein the second communication data is communication data received from the second human user, and wherein the processing the communication data to return sentiment neutral adapted communication data includes replacing a certain phrase defined by the communication data with an alternative phrase, the certain phrase having a threshold exceeding sentiment parameter value.

18. The computer implemented method of claim 1, wherein the presenting to the first human user the adapted second communication includes presenting to the first human user a facial expression gesture by a rendered 3D humanoid model representing a virtual agent.

19. A computer program product comprising:
  a computer readable storage medium readable by one or more processing circuit and storing instructions for execution by one or more processor for performing a method comprising:
    examining communication data of a first human user to return one or more sentiment attribute of the communication data;
    processing the communication data to return sentiment neutral adapted communication data, the processing being in dependence on the one or more sentiment attribute;
    presenting to a second human user a sentiment neutral adapted communication, the sentiment neutral adapted communication being based on the sentiment neutral adapted communication data;
    augmenting second communication data to return adapted second communication data, the augmenting being in dependence on the one or more sentiment attribute; and
    presenting to the first human user an adapted second communication, the adapted second communication being based on the adapted second communication data.

20. A system comprising:
  a memory;
  at least one processor in communication with the memory; and
  program instructions executable by one or more processor via the memory to perform a method comprising:
    examining communication data of a first human user to return one or more sentiment attribute of the communication data;
    processing the communication data to return sentiment neutral adapted communication data, the processing being in dependence on the one or more sentiment attribute;
    presenting to a second human user a sentiment neutral adapted communication, the sentiment neutral adapted communication being based on the sentiment neutral adapted communication data;
    augmenting second communication data to return adapted second communication data, the augmenting being in dependence on the one or more sentiment attribute; and
    presenting to the first human user an adapted second communication, the adapted second communication being based on the adapted second communication data.

\* \* \* \* \*